US011740248B2

United States Patent
Axtell et al.

(10) Patent No.: US 11,740,248 B2
(45) Date of Patent: Aug. 29, 2023

(54) BIOMARKERS FOR ASSESSING SUBJECTS WITH MULTIPLE SCLEROSIS

(71) Applicants: OKLAHOMA MEDICAL RESEARCH FOUNDATION, Oklahoma City, OK (US); THE BOARD OF TRUSTEES OF THE LELAND STANFORD JUNIOR UNIVERSITY, Stanford, CA (US)

(72) Inventors: Robert C. Axtell, Oklahoma City, OK (US); Lawrence Steinman, Stanford, CA (US)

(73) Assignees: OKLAHOMA MEDICAL RESEARCH FOUNDATION, Oklahoma City, OK (US); THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 1354 days.

(21) Appl. No.: 15/763,056

(22) PCT Filed: Sep. 23, 2016

(86) PCT No.: PCT/US2016/053501
§ 371 (c)(1),
(2) Date: Mar. 23, 2018

(87) PCT Pub. No.: WO2017/053838
PCT Pub. Date: Mar. 30, 2017

(65) Prior Publication Data
US 2018/0275145 A1 Sep. 27, 2018

Related U.S. Application Data

(60) Provisional application No. 62/222,707, filed on Sep. 23, 2015.

(51) Int. Cl.
| | |
|---|---|
| *G01N 33/68* | (2006.01) |
| *G16H 50/20* | (2018.01) |
| *G16B 40/30* | (2019.01) |
| *G16B 20/20* | (2019.01) |
| *A61K 38/21* | (2006.01) |
| *G16B 40/00* | (2019.01) |
| *G16B 20/00* | (2019.01) |

(52) U.S. Cl.
CPC ..... *G01N 33/6896* (2013.01); *G01N 33/6863* (2013.01); *G01N 33/6866* (2013.01); *G01N 33/6869* (2013.01); *G01N 33/6893* (2013.01); *G16B 20/20* (2019.02); *G16B 40/30* (2019.02); *G16H 50/20* (2018.01); *A61K 38/215* (2013.01); *G01N 2333/565* (2013.01); *G01N 2800/285* (2013.01); *G01N 2800/52* (2013.01); *G16B 20/00* (2019.02); *G16B 40/00* (2019.02); *Y02A 90/10* (2018.01)

(58) Field of Classification Search
None
See application file for complete search history.

(56) References Cited

U.S. PATENT DOCUMENTS

| | | |
|---|---|---|
| 2010/0167421 A1 | 7/2010 | Rose |
| 2011/0243893 A1 | 10/2011 | Axtell |
| 2011/0294690 A1 | 12/2011 | Montaner Vilallonga |

FOREIGN PATENT DOCUMENTS

| | | |
|---|---|---|
| WO | WO 2007/041245 A2 | 4/2007 |
| WO | WO 2015/023920 A1 | 2/2015 |

OTHER PUBLICATIONS

Tremlett et al. (Journal of Proteomics (2015) vol. 118:p. 2-11; published online Mar. 6, 2015).*
Katsavos et al. (Multiple Sclerosis International (2013) Article id: 340508:20 pages).*
Supplementary European Search Report, Application No. EP 16849780, dated Oct. 21, 2019, 11 pages.
PCT International Search Report & Written Opinion, PCT/US2016/053501, dated Jan. 17, 2017, 20Pages.
O'Connor, P.W. et al., "A Phase II Study of the Safety and Efficacy of Teriflunomide in Multiple Sclerosis with Relapses," Neurology, Mar. 28, 2006, pp. 894-900, vol. 66, No. 6.
Kappas, L. et al., "A Placebo-Controlled Trial of Oral Fingolimod in Relapsing Multiple Sclerosis," The New England Journal of Medicine, Feb. 4, 2010, pp. 387-401, vol. 362, No. 5.
Cohen, J.A. et al, "Oral Fingolimod or Intramuscular Interferon for Relapsing Multiple Sclerosis," The New England Journal of Medicine, Feb. 4, 2010, pp. 402-415, vol. 362, No. 5.

* cited by examiner

*Primary Examiner* — Lori A. Clow

(57) ABSTRACT

Disclosed herein are methods in which an individual with multiple sclerosis (MS) can be classified into one of six subject groups, each subject group predictive for the patient's responsiveness to an interferon-β (IFN-β) therapy. The individual with MS can be classified according to the individual's serum marker levels, e.g., at baseline or following treatment with therapy. Depending on the classification, the individual with MS can be treated with standard therapies (e.g. IFN-β) or one or more alternative therapies with or without IFN-β.

8 Claims, 11 Drawing Sheets

BIOMARKERS FOR ASSESSING SUBJECTS WITH MULTIPLE SCLEROSIS

CROSS REFERENCE TO RELATED APPLICATIONS

This application claims the benefit of U.S. Provisional Application No. 62/222,707, filed Sep. 23, 2015, which is hereby incorporated by reference, in its entirety, for all purposes.

BACKGROUND

Multiple sclerosis (MS) is the most common autoimmune illness of the central nervous system. For many years the inflammatory manifestations of MS were treated using only corticosteroids. However, more recently the results of clinical trials with immunomodulatory agents have changed the therapeutic approach to this disease. Interferon beta (IFNβ)-1b represents the pioneer of those therapies. There is growing evidence from clinical trials on relapsing-remitting MS, primary progressive MS, secondary progressive MS, and clinically isolated syndromes suggestive of MS that IFNβ-1b reduces the frequency and severity of relapses and the development of new and active brain lesions. There can be a significant benefit to treatment early in the disease, for example as shown by the Betaferon/Betaseron in Newly Emerging Multiple Sclerosis For Initial Treatment (BENEFIT) study. Irreversible axonal damage can begin early in the course of MS, and immunomodulatory treatment of MS can have a greater effect early in the disease course.

A downside to this promising therapy is the diversity of responses in patient populations. While a significant proportion of patients can respond to a particular therapy, many do not. The clinician can therefore need to prescribe sequential expensive and time-consuming therapies in order to determine which is effective for the individual patient. Furthermore, it has been reported that IFN-β can exacerbate symptoms in some individuals.

On an individual level, RRMS shows an unpredictable clinical course. Disease heterogeneity extends from clinical course to underlying pathology, where variable pathological patterns are observed in active brain lesions. There is wide variation in treatment response to first-line therapies including recombinant interferon (IFN)-β, the drug class that is widely prescribed for RRMS. IFN-β has modest efficacy in RRMS, reducing relapse rate and disability progression by 30% on average. So far only neutralizing antibodies (NAbs) to IFN-β, which abrogate its bioavailability, have been clearly associated with treatment failure after approximately two years. As NAbs explain only a small number of non-responsiveness, it has been suggested previously that limited efficacy of IFN-β may be due to variations in some as yet unknown characteristics of RRMS patients. Limited efficacy may therefore be a result of treatment populations that are a heterogeneous group of those that respond well to IFN-β therapy and other patients who continue to relapse and accrue disability while on drug.

Many studies have evaluated proteomic, genomic and transcriptomic markers to delineate IFN-β treatment outcome. The majority of studies assessed the statistical significance of a biomarker or series of biomarkers in relation to a clinical outcome of the treatment. A common bifurcated result defined either responders or non-responders by some metric based on clinical relapses and/or disability progression. While this methodology has led to some candidate biomarkers, these studies do not take into account the heterogeneous nature of the RRMS patient population.

The use of disease-modifying therapies in autoimmune conditions is of great clinical interest; however these therapies suffer from the inability to determine a priori which patients will benefit. The present invention addresses this need.

BRIEF DESCRIPTION OF THE SEVERAL VIEWS OF THE DRAWINGS

These and other features, aspects, and advantages of the present invention will become better understood with regard to the following description, and accompanying drawings, where.

SUMMARY

Figure 1:
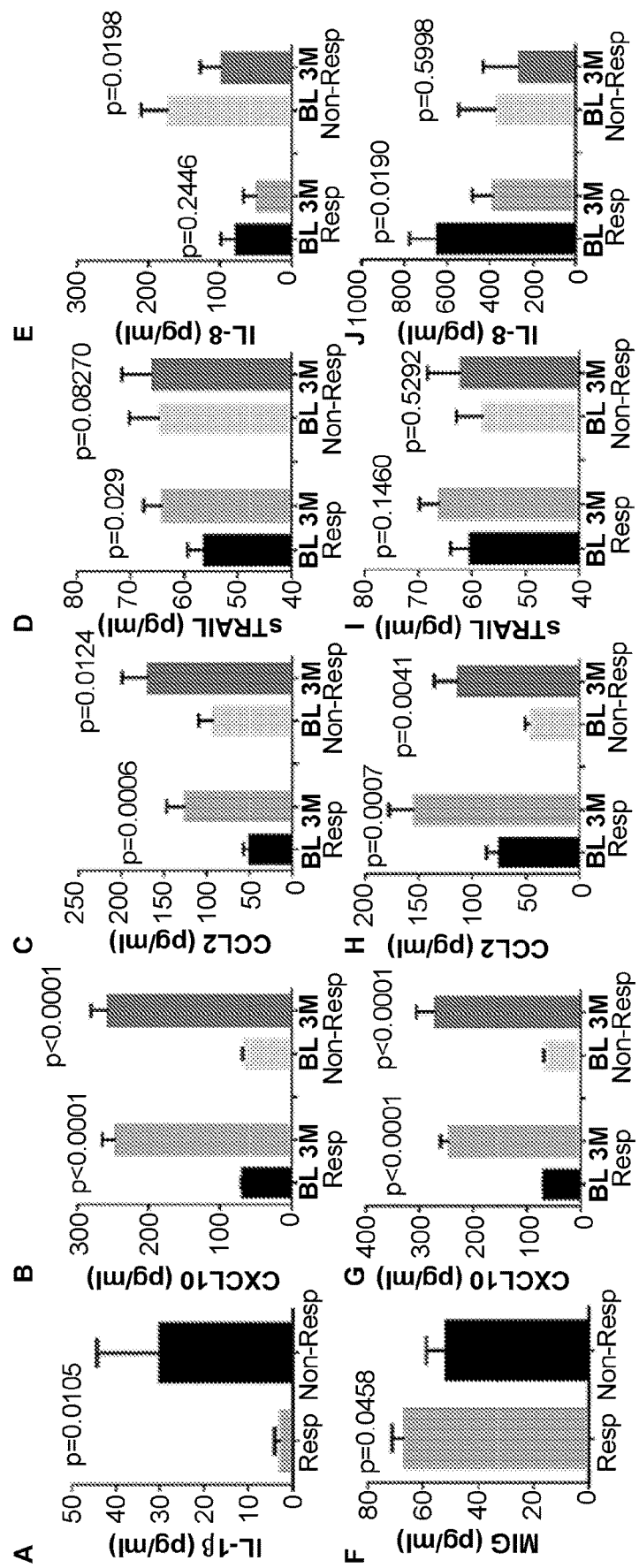
FIGS. 1A-1E depict the comparison of serum cytokines in responders and non-responders defined by relapse at baseline (BL) and 3 months (3M) following treatment with IFN-β. Depicted serum cytokines include (A) IFN-β, (B) CXCL10, (C) CCL2/MCP1 (D) sTRAIL and (E) IL-8.
FIGS. 1F-1J depict the comparison of serum cytokines in responders and non-responders defined by Expanded Disability Status Scale (EDSS) at baseline (BL) and 3 months (3M) following treatment with IFN-β. Depicted serum cytokines include (F) MIG, (G) CXCL10, (H) CCL2/MCP1 (I) sTRAIL and (J) IL-8.

Described herein are methods for prognosing or assessing responsiveness of a subject with MS to a therapy such as IFN. The methods can include classifying the subject in one of a set of classification groups based on the subject's serum biomarker profile. Each classification group can be informative of the subject's responsiveness to a therapy of interest. Methods can further include treatment of the subject in accordance with the prognosis and/or monitoring of the subject following treatment. In some aspects, treatment can be interferon β (IFN-β). In other embodiments, treatment can involve non-IFN-β therapeutics preferably including, but not limited to, glatiramer acetate (Copaxone®), anti-VLA4 (Tysabri®), dimethyl fumarate (Tecfidera®), and teriflunomide (Aubagio®). In particular, it is shown that the subject can be classified into one of at least six distinct groups with respect to the efficacy of immunomodulatory (e.g. IFN-β) treatments of inflammatory diseases in the central nervous system (e.g. multiple sclerosis, neuromyelitis optica, etc.) Multiple sclerosis, in particular relapsing remitting multiple sclerosis (RRMS), primary progressive multiple sclerosis (PPMS), and secondary progressive multiple sclerosis (SPMS) are of particular interest in certain embodiments.

Disclosed herein is a method for prognosing or assessing responsiveness of a subject with multiple sclerosis to treatment with interferon β (IFN-β) comprising: performing or having performed at least one protein biomarker detection assay on a sample from the subject to generate data associated with a panel of biomarkers indicating biomarker expression levels in the sample from the subject, the panel of biomarkers comprising one or more of LIF, IFN-α, IL-1β, IL-8, CCL2/MCP1, IL-1RA, MIP1α, CXCL1/Groα, IL-6, GCSF, IL-10, CD40L, IL-17A, IL-17F, IFN-β, CXCL10/IP10, sTRAIL, PAI-1, CXCL5, HGF, NGF, IL-7, MIG/CXCL9, and VCAM; classifying or having classified the subject into at least one of group 1, group 2, group 3, group 4, group 5, and group 6 based on the generated data associated with the panel of biomarkers; wherein group 1 is characterized by data associated with samples comprising a higher expression level of CD40L in comparison to data associated with samples in group 2; wherein group 2 is characterized by data associated with samples comprising lower or not significantly different expression levels of all biomarkers in the panel of biomarkers in comparison to data associated with samples in groups 1, 3, 4, 5, and 6; wherein group 3 is characterized by data associated with samples comprising higher expression levels of IL-8, CXCL1/Groα, IL-1β, IL-1RA, and CCL2/MCP1 in the panel of biomarkers in comparison to data associated with samples in groups 1, 2, 4, 5, and 6; wherein group 4 is characterized by data associated with samples comprising higher expression levels of G-CSF and CD40L in the panel of biomarkers in comparison to data associated with samples in group 5; wherein group 5 is characterized by data associated with samples comprising higher expression levels of CSCL10/IP10 and IL-6 in the panel of biomarkers in comparison to data associated with samples in group 4; and wherein group 6 is characterized by data associated with samples comprising higher expression levels of IFN-β and IL-17F in the panel of biomarkers in comparison to data associated with samples in groups 1, 2, 3, 4, and 5.

Also disclosed is a method for prognosing or assessing responsiveness of a subject with multiple sclerosis to treatment with IFN-β comprising: obtaining or having obtained data associated with a panel of biomarkers indicating biomarker expression levels in the sample from the subject, the panel of biomarkers comprising one or more of LIF, IFN-α, IL-1-β, IL-8, CCL2/MCP1, IL-1RA, MIP1α, CXCL1/Groα, IL-6, GCSF, IL-10, CD40L, IL-17A, IL-17F, IFN-β, CSCL10/IP10, sTRAIL, PAI-1, CXCL5, HGF, NGF, IL-7, MIG/CXCL9, and VCAM; and classifying or having classified the subject into at least one of group 1, group 2, group 3, group 4, group 5, and group 6 based on the generated data associated with the panel of biomarkers; wherein group 1 is characterized by data associated with samples comprising a higher expression level of CD40L in comparison to data associated with samples in group 2; wherein group 2 is characterized by data associated with samples comprising lower or not significantly different expression levels of all biomarkers in the panel of biomarkers in comparison to data associated with samples in groups 1, 3, 4, 5, and 6; wherein group 3 is characterized by data associated with samples comprising higher expression levels of IL-8, CXCL1/Groα, IL-1β, IL-1RA, and CCL2/MCP1 in the panel of biomarkers in comparison to data associated with samples in groups 1, 2, 4, 5, and 6; wherein group 4 is characterized by data associated with samples comprising higher expression levels of G-CSF and CD40L in the panel of biomarkers in comparison to data associated with samples in group 5; wherein group 5 is characterized by data associated with samples comprising higher expression levels of CSCL10/IP10 and IL-6 in the panel of biomarkers in comparison to data associated with samples in group 4; and wherein group 6 is characterized by data associated with samples comprising higher expression levels of IFNβ and IL-17F in the panel of biomarkers in comparison to data associated with samples in groups 1, 2, 3, 4, and 5.

In some aspects, the at least one biomarker detection assay is a multiplex protein assay.

In some aspects, the panel of biomarkers comprises each of IL-8, CXCL1/Groα, IL-1β, IL-1RA, CCL2/MCP1, IFN-β, IL-17F, CD40L, G-CSF, CXCL10/IP10, and IL-6.

In some aspects, the panel of biomarkers comprises two or more biomarkers and at most eleven biomarkers.

In some aspects, the subject is classified in group 1 or group 5 and based on the classification, further treated with at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof. In some aspects, the subject is classified in group 3 or group 6 and based on the classification, further treated with at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof. In some aspects, the subject is classified in group 2 or group 4 and based on the classification, further treated with at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof.

In some aspects, a method disclosed herein further comprises taking at least one action based on the group into which the subject is classified, optionally wherein the at least one action comprises treating the subject with IFN-β, treating the subject with a therapy other than IFN-β, performing a procedure on the subject, or assessing the subject's health further at another time.

In some aspects, the sample comprises protein from blood of the subject. In some aspects, the sample comprises protein from blood of the subject, the blood of the subject is obtained prior to treatment of the subject with IFN-β. In some aspects, the sample comprises protein from blood of the subject, the blood of the subject is obtained 3 months after beginning treatment of the subject with IFN-β.

In some aspects, the at least one biomarker detection assay is an immunoassay, a protein-binding assay, an antibody-based assay, an antigen-binding protein-based assay, a protein-based array, an enzyme-linked immunosorbent assay (ELISA), flow cytometry, a protein array, a blot, a Western blot, nephelometry, turbidimetry, chromatography, mass spectrometry, enzymatic activity, a radioimmunoassay, immunofluorescence, immunochemiluminescence, immunoelectrochemiluminescence, immunoelectrophoretic, a competitive immunoassay, and immunoprecipitation.

In some aspects, the multiple sclerosis is one of relapsing-remitting multiple sclerosis, primary progressive multiple sclerosis, or secondary progressive multiple sclerosis.

In some aspects, the multiple sclerosis patients in group 1, group 2, group 3, group 4, group 5, and group 6 are derived from multiple sclerosis patients.

In some aspects, each group is previously determined by identifying biomarkers in the samples obtained from the multiple sclerosis patients with a coefficient of variation amongst the samples above 100% and using hierarchical clustering analysis to cluster the multiple sclerosis patients.

In some aspects, the hierarchical clustering analysis to cluster multiple sclerosis patients is conducted using one or more of complete linkage clustering, single linkage clustering, average linkage clustering, centroid linkage clustering, minimum energy clustering, and Ward's method.

Also disclosed herein is a system for prognosing or assessing responsiveness of a subject with multiple sclerosis to treatment with interferon β (IFN-β), comprising: a storage memory for storing a dataset associated with a sample from the subject comprising data associated with a panel of biomarkers indicating biomarker expression levels in the sample from the subject, the panel of biomarkers comprising one or more of LIF, IFNα, IL-1β, IL-8, CCL2/MCP1, IL-1RA, MIP1α, CXCL1/Groα, IL-6, GCSF, IL-10, CD40L, IL-17A, IL-17F, IFNβ, CSCL10/IP10, sTRAIL, PAI-1, CXCL5, HGF, NGF, IL-7, MIG/CXCL9, and VCAM; and a processor communicatively coupled to storage memory for classifying the subject in at least one of group 1, group 2, group 3, group 4, group 5, and group 6 based on the generated data associated with the panel of biomarkers; wherein group 1 is characterized by data associated with samples comprising a higher expression level of CD40L in comparison to data associated with samples in group 2; wherein group 2 is characterized by data associated with samples comprising lower or not significantly different expression levels of all biomarkers in the panel of biomarkers in comparison to data associated with samples in groups 1, 3, 4, 5, and 6; wherein group 3 is characterized by data associated with samples comprising higher expression levels of IL-8, CXCL1/Groα, IL-1β, IL-1RA, and CCL2/MCP1 in the panel of biomarkers in comparison to data associated with samples in groups 1, 2, 4, 5, and 6; wherein group 4 is characterized by data associated with samples comprising higher expression levels of G-CSF and CD40L in the panel of biomarkers in comparison to data associated with samples in group 5; wherein group 5 is characterized by data associated with samples comprising higher expression levels of CSCL10/IP10 and IL-6 in the panel of biomarkers in comparison to data associated with samples in group 4; and wherein group 6 is characterized by data associated with samples comprising higher expression levels of IFNβ and IL-17F in the panel of biomarkers in comparison to data associated with samples in groups 1, 2, 3, 4, and 5.

In some aspects, the system further comprises an apparatus for providing instructions to provide a treatment to the subject with multiple sclerosis based on the group that the subject with multiple sclerosis is classified in, wherein the treatment is one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20, anti-CD52 antibody, IL-17 inhibitor, IL-23 inhibitor, bone marrow stem cell transplantation therapy, or any combination thereof.

In some aspects, the stored dataset comprises data representing expression levels corresponding to each of IL-8, CXCL1/Groα, IL-1β, IL-1RA, CCL2/MCP1, IFN-β, IL-17F, CD40L, G-CSF, CXCL10/IP10, and IL-6.

In some aspects, the stored dataset comprises data representing expression levels corresponding to two or more biomarkers and at most eleven biomarkers.

In some aspects, the subject is classified in group 1 or group 5, and wherein the system further comprises an apparatus for providing instructions to provide a treatment to the subject, the treatment comprising at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof. In some aspects, the subject is classified in group 3 or group 6, and wherein the system further comprises an apparatus for providing instructions to provide a treatment to the subject, the treatment comprising at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof. In some aspects, the subject is classified in group 2 or group 4, and wherein the system further comprises an apparatus for providing instructions to provide a treatment to the subject, the treatment comprising at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof.

In some aspects, the system further comprises an apparatus for providing instructions to take at least one action based on the group into which the subject is classified, optionally wherein the at least one action comprises treating the subject with IFN-β, treating the subject with a therapy other than IFN-β, performing a procedure on the subject, or assessing the subject's health further at another time.

In some aspects, the sample comprises protein from blood of the subject. In some aspects, the sample comprises protein from blood of the subject, the blood of the subject is obtained prior to treatment of the subject with IFN-β. In some aspects, the sample comprises protein from blood of the subject, the blood of the subject is obtained 3 months after beginning treatment of the subject with IFN-β.

In some aspects, the multiple sclerosis is one of relapsing-remitting multiple sclerosis, primary progressive multiple sclerosis, or secondary progressive multiple sclerosis.

In some aspects, the stored dataset associated with the samples characterizing each of group 1, group 2, group 3, group 4, group 5, and group 6 are derived from multiple sclerosis patients. In some aspects, each group is previously determined by identifying biomarkers in the samples obtained from the multiple sclerosis patients with a coefficient of variation amongst the samples above 100% and using hierarchical clustering analysis to cluster the multiple sclerosis patients. In some aspects, the hierarchical clustering analysis to cluster multiple sclerosis patients is conducted using one or more of complete linkage clustering, single linkage clustering, average linkage clustering, centroid linkage clustering, minimum energy clustering, and Ward's method.

Also disclosed herein is a non-transitory computer-readable storage medium storing computer-executable program code for prognosing or assessing responsiveness of a subject with multiple sclerosis to treatment with interferon β (IFN-β), comprising: program code for storing a dataset associated with a sample from the subject comprising data associated with a panel of biomarkers indicating biomarker expression levels in the sample from the subject, the panel of biomarkers comprising one or more of LIF, IFNα, IL-1β, IL-8, CCL2/MCP1, IL-1RA, MIP1α, CXCL1/Groα, IL-6, GCSF, IL-10, CD40L, IL-17A, IL-17F, IFNβ, CSCL10/IP10, sTRAIL, PAI-1, CXCL5, HGF, NGF, IL-7, MIG/CXCL9, and VCAM; and program code for classifying the subject in at least one of group 1, group 2, group 3, group 4, group 5, and group 6 based on the generated data associated with the panel of biomarkers; wherein group 1 is characterized by data associated with samples comprising a higher expression level of CD40L in comparison to data associated with samples in group 2; wherein group 2 is characterized by data associated with samples comprising lower or not significantly different expression levels of all biomarkers in the panel of biomarkers in comparison to data associated with samples in groups 1, 3, 4, 5, and 6; wherein group 3 is characterized by data associated with samples comprising higher expression levels of IL-8, CXCL1/Groα, IL-1β, IL-1RA, and CCL2/MCP1 in the panel of biomarkers in comparison to data associated with samples in groups 1, 2, 4, 5, and 6; wherein group 4 is characterized by data associated with samples comprising higher expression levels of G-CSF and CD40L in the panel of biomarkers in comparison to data associated with samples in group 5; wherein group 5 is characterized by data associated with samples comprising higher expression levels of CSCL10/IP10 and IL-6 in the panel of biomarkers in comparison to data associated with samples in group 4; and wherein group 6 is characterized by data associated with samples comprising higher expression levels of IFNβ and IL-17F in the panel of biomarkers in comparison to data associated with samples in groups 1, 2, 3, 4, and 5.

In some aspects, the non-transitory computer-readable storage medium further comprises computer code that, when executed, provides instructions for treating the subject with multiple sclerosis based on the group that the subject with multiple sclerosis is classified into, wherein the treatment is at least one of IFN-β, glatiramer acetate, natalizumab, dimethyl fumarate, fingolimod, teriflunomide, a statin, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof.

In some aspects, the data associated with the panel of biomarkers comprises each of IL-8, CXCL1/Groα, IL-1β, IL-1RA, CCL2/MCP1, IFN-β, IL-17F, CD40L, G-CSF, CXCL10/IP10, and IL-6. In some aspects, the data associated with the panel of biomarkers comprises two or more biomarkers and at most eleven biomarkers.

In some aspects, the subject is classified in group 1 or group 5 and the computer-readable storage medium further comprises computer code that, when executed, provides instructions for treating the subject with multiple sclerosis based on the classification, the treatment comprising at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof. In some aspects, the subject is classified in group 3 or group 6 and wherein the computer-readable storage medium further comprises computer code that, when executed, provides instructions for treating the subject with multiple sclerosis based on the classification, the treatment comprising at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof. In some aspects, the subject is classified in group 2 or group 4 and wherein the computer-readable storage medium further comprises computer code that, when executed, provides instructions for treating the subject with multiple sclerosis based on the classification, the treatment comprising at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof.

In some aspects, the non-transitory computer-readable storage medium further comprises program code for providing instructions to take at least one action based on the group into which the subject is classified, optionally wherein the at least one action comprises treating the subject with IFN-β, treating the subject with a therapy other than IFN-β, performing a procedure on the subject, or assessing the subject's health further at another time.

In some aspects, the sample comprises protein from blood of the subject. In some aspects, the sample comprises protein from blood of the subject, the blood of the subject is obtained prior to treatment of the subject with IFN-β. In some aspects, the sample comprises protein from blood of the subject, the blood of the subject is obtained 3 months after beginning treatment of the subject with IFN-β.

In some aspects, the multiple sclerosis is one of relapsing-remitting multiple sclerosis, primary progressive multiple sclerosis, or secondary progressive multiple sclerosis.

In some aspects, the data associated with the samples characterizing each of group 1, group 2, group 3, group 4, group 5, and group 6 are derived from multiple sclerosis patients. In some aspects, each group is previously determined by identifying biomarkers in the samples obtained from the multiple sclerosis patients with a coefficient of variation amongst the samples above 100% and using hierarchical clustering analysis to cluster the multiple sclerosis patients. In some aspects, the hierarchical clustering analysis to cluster multiple sclerosis patients is conducted using one or more of complete linkage clustering, single linkage clustering, average linkage clustering, centroid linkage clustering, minimum energy clustering, and Ward's method.

Also disclosed herein is a kit for prognosing and assessing responsiveness of a subject with multiple sclerosis to treatment with interferon β (IFN-β), comprising: a set of reagents for generating a dataset via at least one biomarker detection assay that is associated with a sample from the subject comprising data associated with a panel of biomarkers indicating biomarker expression levels in the sample from the subject, the panel of biomarkers comprising one or more of LIF, IFNα, IL-1β, IL-8, CCL2/MCP1, IL-1RA, MIP1α, CXCL1/Groα, IL-6, GCSF, IL-10, CD40L, IL-17A, IL-17F, IFNβ, CSCL10/IP10, sTRAIL, PAI-1, CXCL5, HGF, NGF, IL-7, MIG/CXCL9, and VCAM; and instructions for classifying the subject in at least one of group 1, group 2, group 3, group 4, group 5, and group 6 based on the generated data associated with the panel of biomarkers; wherein group 1 is characterized by data associated with samples comprising a higher expression level of CD40L in comparison to data associated with samples in group 2; wherein group 2 is characterized by data associated with samples comprising lower or not significantly different expression levels of all biomarkers in the panel of biomarkers in comparison to data associated with samples in groups 1, 3, 4, 5, and 6; wherein group 3 is characterized by data associated with samples comprising higher expression levels of IL-8, CXCL1/Groα, IL-1RA, and CCL2/MCP1 in the panel of biomarkers in comparison to data associated with samples in groups 1, 2, 4, 5, and 6; wherein group 4 is characterized by data associated with samples comprising higher expression levels of G-CSF and CD40L in the panel of biomarkers in comparison to data associated with samples in group 5; wherein group 5 is characterized by data associated with samples comprising higher expression levels of CSCL10/IP10 and IL-6 in the panel of biomarkers in comparison to data associated with samples in group 4; and wherein group 6 is characterized by data associated with samples comprising higher expression levels of IFNβ and IL-17F in the panel of biomarkers in comparison to data associated with samples in groups 1, 2, 3, 4, and 5.

In some aspects, kit further comprises instructions for providing a treatment to the subject with multiple sclerosis based on the group that the subject with multiple sclerosis is classified in, wherein the treatment is one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof.

In some aspects, the at least one biomarker detection assay is a multiplex protein assay.

In some aspects, the panel of biomarkers comprises each of IL-8, CXCL1/Groα, IL-1β, IL-1RA, CCL2/MCP1, IFN-β, IL-17F, CD40L, G-CSF, CXCL10/IP10, and IL-6. In some aspects, the panel of biomarkers comprises two or more biomarkers and at most eleven biomarkers.

In some aspects, the subject is classified in group 1 or group 5, and the kit further comprises instructions for providing a treatment to the subject with multiple sclerosis based on the classification, the treatment comprising at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof. In some aspects, the subject is classified in group 3 or group 6, and the kit further comprises instructions for providing a treatment to the subject with multiple sclerosis based on the classification, the treatment comprising at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof. In some aspects, the subject is classified in group 2 or group 4, and the kit further comprises instructions for providing a treatment to the subject with multiple sclerosis based on the classification, the treatment comprising at least one of IFN-β, glatiramer acetate, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, bone marrow stem cell transplantation therapy, or any combination thereof.

In some aspects, the kit further comprises instructions for taking at least one action based on the group into which the subject is classified, optionally wherein the at least one action comprises treating the subject with IFN-β, treating the subject with a therapy other than IFN-β, performing a procedure on the subject, or assessing the subject's health further at another time.

In some aspects, the sample comprises protein from blood of the subject. In some aspects, the sample comprises protein from blood of the subject, the blood of the subject is obtained prior to treatment of the subject with IFN-β. In some aspects, the sample comprises protein from blood of the subject, the blood of the subject is obtained 3 months after beginning treatment of the subject with IFN-β.

In some aspects, the at least one biomarker detection assay is an immunoassay, a protein-binding assay, an antibody-based assay, an antigen-binding protein-based assay, a protein-based array, an enzyme-linked immunosorbent assay (ELISA), flow cytometry, a protein array, a blot, a Western blot, nephelometry, turbidimetry, chromatography, mass spectrometry, enzymatic activity, a radioimmunoassay, immunofluorescence, immunochemiluminescence, immunoelectrochemiluminescence, immunoelectrophoretic, a competitive immunoassay, and immunoprecipitation.

In some aspects, the multiple sclerosis is one of relapsing-remitting multiple sclerosis, primary progressive multiple sclerosis, or secondary progressive multiple sclerosis.

In some aspects, the data associated with the samples characterizing each of group 1, group 2, group 3, group 4, group 5, and group 6 are derived from multiple sclerosis patients. In some aspects, each group is previously determined by identifying biomarkers in the samples obtained from the multiple sclerosis patients with a coefficient of variation amongst the samples above 100% and using hierarchical clustering analysis to cluster the multiple sclerosis patients. In some aspects the hierarchical clustering analysis to cluster multiple sclerosis patients is conducted using one or more of complete linkage clustering, single linkage clustering, average linkage clustering, centroid linkage clustering, minimum energy clustering, and Ward's method.

DETAILED DESCRIPTION

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise.

A "subject" in the context of the present teachings is generally a mammal, e.g., a human. The subject can be a human patient, e.g., a MS patient. The term "mammal" as used herein includes but is not limited to a human, non-human primate, dog, cat, mouse, rat, cow, horse, and pig. Mammals other than humans can be advantageously used as subjects that represent animal models of, e.g. MS. A subject can be male or female. A subject can be one who has been previously diagnosed or identified as having MS. A subject can be one who has already undergone, or is undergoing, a therapeutic intervention for MS. A subject can also be one who has not been previously diagnosed as having MS; e.g., a subject can be one who exhibits one or more symptoms or risk factors for MS, or a subject who does not exhibit symptoms or risk factors for MS, or a subject who is asymptomatic for MS.

The term "inflammatory" response is the development of a humoral (antibody mediated) and/or a cellular (mediated by antigen-specific T cells or their secretion products) response. An "immunogen" is capable of inducing an immunological response against itself on administration to a mammal or due to autoimmune disease.

The terms "biomarker," "biomarkers," "marker" or "markers" refer to, without limitation, cytokines, chemokines, growth factors, proteins, peptides, nucleic acids, oligonucleotides, and metabolites, together with their related metabolites, mutations, variants, polymorphisms, modifications, fragments, subunits, degradation products, elements, and other analytes or sample-derived measures. Markers can also include mutated proteins, mutated nucleic acids, variations in copy numbers and/or transcript variants. Markers also encompass non-blood borne factors and non-analyte physiological markers of health status, and/or other factors or markers not measured from samples (e.g., biological samples such as bodily fluids), such as clinical parameters and traditional factors for clinical assessments. Markers can also include any indices that are calculated and/or created mathematically. Markers can also include combinations of any one or more of the foregoing measurements, including temporal trends and differences.

Biomarkers such as cytokines are messenger molecules produced by B cells, T cells, macrophage, dendritic cells and other immune and host cells. Cytokines play roles in the pathogenesis of inflammatory diseases, including without limitation multiple sclerosis, neuromyelitis optica, and the like. Cytokines include chemokines, lymphokines, growth factors, angiogenesis factors, and other secreted and cell surface molecules that transmit signals to other cells. Markers of the present methods include cytokines.

Various markers are shown in the tables. Markers can include PDGFBB, sFAS ligand, M-CSF, TNF-β, IFNα, IL-1RA, MCP-1, IL-2, IL-6, IL-8, FGFb, IL-7, MIG/CXCL9, TGF-βIFNβ, IL-13, IL-17F, EOTAXIN, IL-1α, MCP-3, LIF, NGF, RANTES, IL-5, MIP1β, IL-12p70, and/or HGF. Additionally, markers can include LIF, IFNα, CCL2/MCP1, IL-1RA, MIP1α, CXCL1/Groα, IL-6, GCSF, IL-10, CD40L, IL-17A, IL-17F, IFNβ, CSCL10/IP10, sTRAIL, PAI-1, CXCL5, and VCAM.

To "analyze" includes determining a set of values associated with a sample by measurement of a marker (such as, e.g., presence or absence of a marker or constituent expression levels) in the sample and comparing the measurement against measurement in a sample or set of samples from the same subject or other control subject(s). The markers of the present teachings can be analyzed by any of various conventional methods known in the art. To "analyze" can include performing a statistical analysis to, e.g., determine whether a subject is a responder or a non-responder to a therapy (e.g., an IFN treatment as described herein).

A "sample" in the context of the present teachings refers to any biological sample that is isolated from a subject, e.g., a blood sample. A sample can include, without limitation, a single cell or multiple cells, fragments of cells, an aliquot of body fluid, whole blood, platelets, serum, plasma, red blood cells, white blood cells or leucocytes, endothelial cells, tissue biopsies, synovial fluid, lymphatic fluid, ascites fluid, and interstitial or extracellular fluid. The term "sample" also encompasses the fluid in spaces between cells, including gingival crevicular fluid, bone marrow, cerebrospinal fluid (CSF), saliva, mucous, sputum, semen, sweat, urine, or any other bodily fluids. "Blood sample" can refer to whole blood or any fraction thereof, including blood cells, red blood cells, white blood cells or leukocytes, platelets, serum and plasma. Samples can be obtained from a subject by means including but not limited to venipuncture, excretion, ejaculation, massage, biopsy, needle aspirate, lavage, scraping, surgical incision, or intervention or other means known in the art.

A "dataset" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored. Similarly, the term "obtaining a dataset associated with a sample" encompasses obtaining a set of data determined from at least one sample. Obtaining a dataset encompasses obtaining a sample, and processing the sample to experimentally determine the data, e.g., via measuring, PCR, microarray, one or more primers, one or more probes, antibody binding, or ELISA. The phrase also encompasses receiving a set of data, e.g., from a third party that has processed the sample to experimentally determine the dataset. Additionally, the phrase encompasses mining data from at least one database or at least one publication or a combination of databases and publications.

"Measuring" or "measurement" in the context of the present teachings refers to determining the presence, absence, quantity, amount, or effective amount of a substance in a clinical or subject-derived sample, including the presence, absence, or concentration levels of such substances, and/or evaluating the values or categorization of a subject's clinical parameters based on a control.

Classification can be made according to predictive modeling methods that set a threshold for determining the probability that a sample belongs to a given class. The probability preferably is at least 50%, or at least 60% or at least 70% or at least 80% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. area under the curve (AUC) or accuracy, of a particular value, or range of values. In some embodiments, a desired quality threshold is a predictive model that will classify a sample with an accuracy of at least about 0.7, at least about 0.75, at least about 0.8, at least about 0.85, at least about 0.9, at least about 0.95, or higher. As an alternative measure, a desired quality threshold can refer to a predictive model that will classify a sample with an AUC (area under the curve) of at least about 0.7, at least about 0.75, at least about 0.8, at least about 0.85, at least about 0.9, or higher.

As is known in the art, the relative sensitivity and specificity of a predictive model can be "tuned" to favor either the selectivity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about at least about 0.7, at least about 0.75, at least about 0.8, at least about 0.85, at least about 0.9, or higher.

Methods

Disclosed herein are various methods for prognosing and assessing multiple sclerosis patients for their ability to respond to immunomodulatory therapies (e.g. IFN-β) using marker signature patterns at baseline and post therapy (e.g. 3 months post-treatment). Marker signature pattern as used herein refers to the spectrum of biomarker levels, which frequently are serum levels of biomarkers, including without limitation cytokine biomarkers. Once the marker levels and pattern for a particular sample are identified, the individual from which the particular sample was derived from is classified in a subject group, and the classification is used in selecting the most appropriate therapy for an individual. By analysis of marker levels on an individual basis, the specific subclass of disease is determined, and the patient can be classified based on the likelihood to respond to treatments of interest, including treatment with interferons, cytokines, cytokine antagonists, cytokine mimetics and bioequivalents, steroids, NSAIDs, statins, and the like, including IFN-β, anti-IL-17, particularly IL-17F, anti-IL-23, IFN-γ, etc. Thus, the marker signature can provide prognostic information to guide clinical decision making, both in terms of institution of and escalation of therapy as well as in the selection of the therapeutic agent to which the patient is most likely to exhibit a robust response. For example, the information obtained from the biomarker (e.g. cytokine) profile is used to optimize the selection of therapeutic agents. With this approach, therapeutic regimens can be individualized and tailored according to the specificity data obtained at different times over the course of treatment, thereby providing a regimen that is individually appropriate. In addition, patient samples can be obtained at any point during the treatment process for analysis.

Classification of a Subject with Multiple Sclerosis

Disclosed herein are methods for classifying a subject with MS into a classification group and, in some instances, subsequently taking an action based on the classification group the subject is classified in.

In general, such methods for classifying a subject with MS involve determining the presence or level of cytokines in an individual sample derived from the subject with MS. Samples can be obtained from the tissues or fluids of an individual. For example, samples can be obtained from whole blood, tissue biopsy, serum, etc. Other sources of samples are body fluids such as lymph, cerebrospinal fluid, and the like. Also included in the term are derivatives and fractions of such cells and fluids. Diagnostic samples are collected any time after an individual is suspected to have an inflammatory disease or has exhibited symptoms that predict such a disease.

In the methods of the invention, relevant cytokines for analysis of a subject with MS include, without limitation, one or more of LIF, IFNα, IL-1β, IL-8, CCL2/MCP1, IL-1RA, MIP1α, CXCL1/Groα, IL-6, GCSF, IL-10, CD40L, IL-17A, IL-17F, IFN, CSCL10/IP10, sTRAIL, PAI-1, CXCL5, HGF, NGF, IL-7, MIG/CXCL9, and VCAM. These may be referred to as a cytokine panel or a biomarker panel. In some embodiments, panel of biomarkers includes each of IL-8, CXCL1/Groα, IL-1β, IL-1RA, CCL2/MCP1, IFN-β, IL-17F, CD40L, G-CSF, CXCL10/IP10, and IL-6. In some embodiments, a minimum of two biomarkers is used in the panel of biomarkers to effectively classify a subject with MS.

The measurement of markers in an individual sample may use one or more affinity reagents specific for the defined panel of markers; physically contacting the panel with the individual patient sample such as blood, serum, plasma, etc.; identifying and quantitating the markers that bind to the panel; and determining the classification based on criteria provided herein. A variety of different assays can be utilized to quantitate the presence of such markers. For example, the biomarker measurements described herein can be conducted using ProcartaPlex® Multiplex Immunoassays purchasable from eBiosciences/Affymetrix. Examples include the ProcartaPlex® Human 45plex Control Set (catalog number: EPX450-12171-CTR), ProcartaPlex® Human Cytokine and Chemokine Panel 1A (34 plex) (catalog number: EPX340-12167-901), and/or a custom Panel Configurator at www.ebioscience.com including the biomarkers described herein. Further discussion regarding the assays is described below.

The classification can be generated from a biological sample using any convenient protocol. The readout can be a mean, average, median or the variance or other statistically or mathematically-derived value associated with the measurement. The marker readout information can be further refined by direct comparison with the corresponding reference or control pattern. A binding pattern can be evaluated on a number of points: to determine if there is a statistically significant change at any point in the data matrix; whether the change is an increase or decrease in the binding; whether the change is specific for one or more physiological states, and the like. The absolute values obtained for each marker under identical conditions will display a variability that is inherent in live biological systems and also reflects the variability inherent between individuals.

Following obtainment of the marker measurements from the sample being assayed, the signature pattern can be compared with a reference or control profile to classify the patient from which the sample was obtained/derived. In various embodiments, a patient with MS is classified into one of 6 distinct patient groups. Therefore, the marker measurements derived from the patient with MS can be compared to reference levels that previously characterize each of the 6 distinct patient groups. Typically a comparison is made with a sample or set of samples from a patient population, and can further comprise comparison with an unaffected, normal source. Additionally, a reference or control signature pattern can be a signature pattern that is obtained from a sample of a patient known to be responsive or non-responsive to the therapy of interest, and therefore can be a positive reference or control profile. A patient can then be classified based on the levels of various markers in a sample obtained from the patient in comparison to marker levels in healthy and/or other patients with MS.

As referred to below, each group can be characterized by individuals with marker levels that are described as "higher," "lower," or "not significantly different" from marker levels of individuals in other groups. The comparative differences in individual marker levels in the resulting groups is determined using statistical analysis; namely, the statistical analysis is conducted using a Kruskal-Wallis test with a Dunn's multiple comparisons test in Prism version 6 (GraphPad Software, Inc., La Jolla, Calif.).

At baseline:
Group 1 has higher expression levels of CD40L compared to Group 2, and lower or not significantly different levels of all other cytokines in the cytokine panel as compared to Groups 3, 4, 5, and 6.
Group 2 has lower or not significantly different levels of all cytokines in the panel as compared to Groups 1, 3, 4, 5, and 6.
Group 3 has higher levels of IL-8, Groα, IL-1RA and MCP1 compared to Groups 1, 2, 4, 5, and 6.
Group 4 has higher levels of G-CSF and CD40L compared to Group 5.
Group 5 has higher levels of Groα and IL-6 compared to Group 4.
Group 6 has higher levels of IFN-β and IL-17F compared to Groups 1, 2, 3, 4, and 5.

In some aspects, a subject with MS can be classified in a group by observing the marker levels of at least 2, 3, 4, 5, 6, 7, 8, 9, 10, 11, or 12 markers. For example, if a subject with MS presents with elevated baseline serum levels of IFN-β and IL-17F, the subject can be classified in Group 6. As another example, observing the marker levels of three cytokines is sufficient to classify a subject. If a subject with MS presents with elevated baseline serum levels of IL-8, IL-1β, and MCP1, the subject can be classified in Group 3. For accurate classification of a subject with MS in Groups 1, 2, 4, and 5, the full panel of biomarkers (e.g. including at least IL-8, CXCL1/Groα, IL-1β, IL-1RA, CCL2/MCP1, IFN-β, IL-17F, CD40L, G-CSF, CXCL10/IP10, and IL-6) can be used. In some aspects, a marker level from a subject with MS is deemed "elevated" if it is statistically significantly higher than the marker level from samples obtained from healthy subjects.

The responsiveness of patients in each group can be prognosed as follows, where a "+" sign is indicative of responsiveness, or lack of increase in EDSS score (i.e. a "−" indicates lack of responsiveness as measured by EDSS score)

Responsiveness to IFN-β by EDSS score
Group 1: +
Group 2: −
Group 3: not significant
Group 4: not significant
Group 5: +
Group 6: −

Responsiveness to IFN-β by relapse rate
Group 1: ++
Group 2: +
Group 3: −
Group 4: +
Group 5: ++
Group 6: −

These data indicate that an individual classified as Group 1 or Group 5 can be predicted to respond well to treatment with IFN-β while individuals in Group 3 and 6 are not responsive to IFN-β. This may be attributed to the indication of a strong TH17 response in these patients in Group 3 and Group 6. Individuals classified in Group 2 or Group 4 are a mix of responders and non-responders to IFN-β. Therefore, patients classified in these groups have different options for treatment.

Individuals that respond to therapy can also be stratified into groups based on changes in marker levels following administration of IFN-β, for example at a period of from about one to 4 months following initiation of therapy. For example, responsive individuals (based on EDSS) can show a decrease in serum levels of IL-8, plasminogen activator inhibitor 1 (PAI), CXCL5 and hepatocyte growth factor (HGF), CD40L, IL-17A and NGF. Therefore, a subject with MS that has undergone treatment with IFN-β and presents, at 3 months post-treatment, with decreased serum marker levels of IL-8, PAI, CXCL5, HGF, CD40L, IL-17A, and NGF can be classified in Group 1 or Group 5. In some aspects, a marker level from a subject with MS is deemed "decreased" if it is statistically significantly lower than the marker levels from healthy subjects. In other aspects, the measurements can be made relative to a predetermined standard based on patient samples, or compared to a plurality of MS patients, e.g. 1, 5, 10, 15, 20 25, 30, 35, 40, 45, 50 or more patients.

In other aspects, responsive individuals (based on relapse rates) can show, at 3 months post-treatment, elevated levels of sTRAIL, G-CSF, TGFβ, ICAM, IL-12p40, MIP1β, CD40L, IL-1RA and MIP1α. Therefore, a subject with MS can be classified in Group 1 or Group 5 if, at 3 months post-treatment with IFN-β, the patient shows elevated levels of sTRAIL, G-CSF, TGFβ, ICAM, IL-12p40, MIP1β, CD40L, IL-1RA and MIP1α.

Non-responders (based on EDSS) can show a significant increase in VCAM. Therefore, a subject with MS that has undergone treatment with IFN-β and presents, at 3 months post-treatment, with elevated VCAM, can be classified in Group 3 or Group 6.

In other aspects, non-responsive individuals (based on relapse rates) can show, at 3 months post-treatment, statistically decreased levels of IL-8 and statistically increased levels of IFN-α and TNFβ. Therefore, a subject with MS can be classified in Group 3 or Group 6 if, at 3 months post-treatment with IFN-β, the patient shows decreased levels of IL-8 and/or elevated levels of IFN-α and TNFβ.

Therefore, the methods of the invention allow for classification of MS patients where there is a high degree of heterogeneity and variation in the levels of markers, and the methods also account for differences in responsiveness depending on how the end point is defined, i.e., according to change in EDSS score or according to the presence of relapses. This classification allows improved care, where patients classified can be treated with an appropriate agent, as described further below.

Therapy Based on Patient Classification

In the treatment of inflammatory central nervous system disorders, IFN-β and similar drugs can be advised or provided for patients classified in Groups 1 or 5 (e.g., responders), while patients classified in Groups 3 or 6 (e.g., non-responders) can be treated with alternative therapeutic agents (e.g. glatiramer acetate (Copaxone®), anti-VLA4 (Tysabri®), dimethyl fumarate (Tecfidera®), and teriflunomide (Aubagio®)). Additionally, patients classified in Groups 2 or 4 can be treated with IFN-β and similar drugs, with any of the aforementioned alternative therapeutic agents, or any combination thereof.

As previously discussed, a MS patient can be classified in one of the six subject groups, each subject group characterized by baseline or post-treatment biomarker levels from a panel of biomarkers. Depending on the classification, at least one action can be taken such as treating the subject or instructing/recommending treatment of the subject with a particular therapy or therapies. For example, the at least one action can be a treatment with IFN-β. As another example, the one action can be a treatment with a therapy other than IFN-β. Other actions include performing a procedure on the subject (e.g. bone marrow stem cell transplant). Another action includes choosing to assess the MS patient's health again at a subsequent time.

As previous described, MS patients classified in group 1 or group 5 demonstrate responsiveness to IFN-β treatment. Therefore, a MS patient that is classified in group 1 or group 5 based on his/her baseline marker levels can be treated with IFN-β. In some embodiments, a patient classified in subject group 1 or group 5 can be treated with alternative therapies alone or in combination with IFN-β. Alternative therapies can include glatiramer acetate, natalizumab, dimethyl fumarate, fingolimod, teriflunomide, a statin, methylprednisolone, methotrexate, cladribine, cyclophosphamide, anti-IFN γ antibody, CTLA4-Ig, anti-CD20 antibody (e.g., rituximab or ocreluzimab), anti-CD52 antibody (e.g., alemtuzumab), IL-17 inhibitor (e.g., secukinumab, ixekuzumab, or brodalumab), IL-23 inhibitor (e.g., ustekinumab), and/or bone marrow stem cell transplantation therapy.

Patients in subject groups 3 and 6 are typically non-responsive to IFN-β treatment. Therefore, alternative therapies in addition to, or in replacement of IFN-β can be useful. Preferable alternative therapeutics include glatiramer acetate (Copaxone®), anti-VLA4 (Tysabri®), dimethyl fumarate (Tecfidera®), and teriflunomide (Aubagio®). In some embodiments, MS patients in group 3 or group 6 can be additionally treated with fingolimod, statins, methylprednisolone, methotrexate, cladribine, cyclophosphamide, anti-IFN γ antibody, CTLA4-Ig, anti-CD20 antibody (e.g., rituximab or ocreluzimab), anti-CD52 antibody (e.g., alemtuzumab), IL-17 inhibitor (e.g., secukinumab, ixekuzumab, or brodalumab), IL-23 inhibitor (e.g., ustekinumab), or bone marrow stem cell transplantation therapy. MS patients classified in group 3 or group 6 can demonstrate increased responsiveness to one or more of these alternative therapeutics in comparison to IFN-β.

Patients in subject group 2 and group 4 can demonstrate a level of responsiveness to IFN-β that falls between the responsiveness exhibited by patients of Groups 1/5 and patients of Groups 3/6. In various embodiments, a MS patient that is classified in group 2 or group 4 can be treated with IFN-β. In other embodiments, a MS patient classified in group 2 or group 4 can be treated with an alternative therapy in addition to or in place of IFN-β, which can include glatiramer acetate (Copaxone®), anti-VLA4 (Tysabri®), dimethyl fumarate (Tecfidera®), or teriflunomide (Aubagio®). In another embodiment, a MS patient classified in group 2 or group 4 may be treated with fingolimod, a statin (e.g., simvastatin) methylprednisolone, methotrexate, cladribine, cyclophosphamide, anti-IFN γ antibody, CTLA4-Ig (e.g., abatacept or belatacept), anti-CD20 antibody (e.g., rituximab or ocreluzimab), anti-CD52 antibody (e.g., alemtuzumab), IL-17 inhibitor (e.g., secukinumab, ixekuzumab, or brodalumab), IL-23 inhibitor (e.g., ustekinumab), or bone marrow stem cell transplantation therapy. In yet another embodiment, a MS patient classified in group 2 or group 4 can be treated with any combination of the aforementioned therapeutics.

Assays

Many assays are known to one of skill in the art, including ELISA, protein arrays, eTag system, bead based systems, tag or other array based systems etc. Examples of such methods are set forth in the art, including, inter alia, chip-based capillary electrophoresis: Colyer et al. (1997) J Chromatogr A. 781(1-2):271-6; mass spectroscopy: Petricoin et al. (2002) Lancet 359: 572-77; eTag systems: Chan-Hui et al. (2004) Clinical Immunology 111:162-174; microparticle-enhanced nephelometric immunoassay: Montagne et al. (1992) Eur J Clin Chem Clin Biochem. 30(4):217-22; antigen arrays: Robinson et al. (2002) Nature Medicine, 8:295-301; the Luminex XMAP bead array system; and the like, each of which are herein incorporated by reference. Detection can utilize one or a panel of specific binding members, e.g. a panel or cocktail of binding members specific for one, two, three, four, five or more markers.

Additional examples of assays for one or more markers include DNA assays, microarrays, polymerase chain reaction (PCR), RT-PCR, Southern blots, Northern blots, antibody-binding assays, enzyme-linked immunosorbent assays (ELISAs), flow cytometry, protein assays, Western blots, nephelometry, turbidimetry, chromatography, mass spectrometry, immunoassays, including, by way of example, but not limitation, RIA, immunofluorescence, immunochemiluminescence, immunoelectrochemiluminescence, or competitive immunoassays, immunoprecipitation, and the assays described in the Examples section below. The information from the assay can be quantitative and sent to a computer system of the invention. The information can also be qualitative, such as observing patterns or fluorescence, which can be translated into a quantitative measure by a user or automatically by a reader or computer system.

Various immunoassays designed to quantitate markers can be used in screening including multiplex assays. Measuring the concentration of the target protein in a sample or fraction thereof can be accomplished by a variety of specific assays. For example, a conventional sandwich type assay can be used in an array, ELISA, RIA, etc. format. Other immunoassays include Ouchterlony plates that provide a simple determination of antibody binding. Additionally, Western blots can be performed on protein gels or protein spots on filters, using a detection system specific for the markers as desired, conveniently using a labeling method.

For multiplex analysis of markers, arrays containing one or more anti-cytokine affinity reagents, e.g. antibodies can be generated. Such an array can be constructed comprising antibodies against markers.

Arrays provide a high throughput technique that can assay a large number of markers in a sample. Arrays can be created by spotting a probe onto a substrate (e.g., glass, nitrocellulose, etc.) in a two-dimensional matrix or array having bound probes. The probes can be bound to the substrate by either covalent bonds or by non-specific interactions, such as hydrophobic interactions. Techniques for constructing arrays and methods of using these arrays are described in, for example, Schena et al. (1996) *Proc Natl Acad Sci USA*. 93(20):10614-9; Schena et al. (1995) *Science* 270(5235): 467-70; Shalon et al. (1996) *Genome Res.* 6(7):639-45, U.S. Pat. No. 5,807,522, EP 799 897; WO 97/29212; WO 97/27317; EP 785 280; WO 97/02357; U.S. Pat. Nos. 5,593,839; 5,578,832; EP 728 520; U.S. Pat. No. 5,599,695; EP 721 016; U.S. Pat. No. 5,556,752; WO 95/22058; and U.S. Pat. No. 5,631,734.

Protein based analysis, using an antibody as described above that specifically binds to a polypeptide (e.g. biomarker), can be used to quantify the biomarker level in a test sample obtained from a patient with MS. In one aspect, the level or amount of a biomarker in a sample obtained from a patient with MS is compared with the level or amount of the biomarker in a control sample obtained from a patient without MS. In other aspects, the level or amount of a biomarker in a sample obtained from a first patient with MS is compared with the level or amount of the biomarker in a sample obtained from a second patient with MS. A level or amount of the biomarker in the sample from a first patient that is higher or lower than the level or amount of the biomarker in the sample from the second patient, such that the difference is statistically significant, is indicative of different classifications (e.g. Group 1-6) of the first patient and second patient with MS.

Assessment of Patient Outcomes

Patient outcomes and responder status can be assessed using imaging-based criteria such as radiographic scores, clinical and laboratory criteria. Multiple different imaging, clinical and laboratory criteria and scoring systems have been and are being developed to assess disease activity and response to therapy in inflammatory diseases, including without limitation inflammatory demyelinating disease, e.g. multiple sclerosis, neuromyelitis optica, etc.

A responder or non-responder pattern can be obtained as a dataset. The dataset comprises quantitative data for the presence in serum of a panel of cytokine markers as defined herein. The dataset optionally quantitative data for the presence in a clinical sample of other markers, including T cell presence or specificity, clinical indices, and the like. Clinical factors are described in more detail below.

In order to identify profiles that are indicative of responsiveness, a statistical test will provide a confidence level for a change in the expression, titers or concentration of markers between the test and control profiles to be considered significant, where the control profile can be for responsiveness or non-responsiveness. The raw data can be initially analyzed by measuring the values for each marker, usually in duplicate, triplicate, quadruplicate or in 5-10 replicate features per marker.

A test dataset is considered to be different than a control dataset if one or more of the parameter values of the profile exceeds the limits that correspond to a predefined level of significance.

To provide significance ordering, the false discovery rate (FDR) can be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001) PNAS 98, 5116-21, herein incorporated by reference). This analysis algorithm is currently available as a software "plug-in" for Microsoft Excel know as Significance Analysis of Microarrays (SAM). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value can be applied to the correlations between experimental profiles.

For SAM, Z-scores represent another measure of variance in a dataset, and are equal to a value of X minus the mean of X, divided by the standard deviation. A Z-Score tells how a single data point compares to the normal data distribution. A Z-score demonstrates not only whether a datapoint lies above or below average, but how unusual the measurement is. The standard deviation is the average distance between each value in the dataset and the mean of the values in the dataset.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data can be subjected to non-supervised hierarchical clustering to reveal relationships among profiles. For example, hierarchical clustering can be performed, where the Pearson correlation is employed as the clustering metric. One approach is to consider a patient disease dataset as a "learning sample" in a problem of "supervised learning". CART is a standard in applications to medicine (Singer (1999) Recursive Partitioning in the Health Sciences, Springer), which can be modified by transforming any qualitative features to quantitative features; sorting them by attained significance levels, evaluated by sample reuse methods for Hotelling's $T^2$ statistic; and suitable application of the lasso method. Problems in prediction are turned into problems in regression without losing sight of prediction, indeed by making suitable use of the Gini criterion for classification in evaluating the quality of regressions.

Other methods of analysis that can be used include logic regression. One method of logic regression Ruczinski (2003) Journal of Computational and Graphical Statistics 12:475-512. Logic regression resembles CART in that its classifier can be displayed as a binary tree. It is different in that each node has Boolean statements about features that are more general than the simple "and" statements produced by CART.

Another approach is that of nearest shrunken centroids (Tibshirani (2002) PNAS 99:6567-72). The technology is k-means-like, but has the advantage that by shrinking cluster centers, one automatically selects features (as in the lasso) so as to focus attention on small numbers of those that are informative. The approach is available as Prediction Analysis of Microarrays (PAM) software, a software "plug-in" for Microsoft Excel, and is widely used. Two further sets of algorithms are random forests (Breiman (2001) Machine Learning 45:5-32 and MART (Hastie (2001) The Elements of Statistical Learning, Springer). These two methods are already "committee methods." Thus, they involve predictors that "vote" on outcome. Several of these methods are based on the "R" software, developed at Stanford University, which provides a statistical framework that is continuously being improved and updated in an ongoing basis.

Other statistical analysis approaches including principle components analysis, recursive partitioning, predictive algorithms, Bayesian networks, and neural networks.

These tools and methods can be applied to several classification problems. For example, methods can be developed from the following comparisons: i) all cases versus all controls, all cases versus nonresponsive controls, iii) all cases versus responsive controls.

In a second analytical approach, variables chosen in the cross-sectional analysis are separately employed as predictors. Given the specific outcome, the random lengths of time each patient will be observed, and selection of proteomic and other features, a parametric approach to analyzing responsiveness can be better than the widely applied semi-parametric Cox model. A Weibull parametric fit of survival permits the hazard rate to be monotonically increasing, decreasing, or constant, and also has a proportional hazards representation (as does the Cox model) and an accelerated failure-time representation. All the standard tools available in obtaining approximate maximum likelihood estimators of regression coefficients and functions of them are available with this model.

In addition the Cox models can be used, especially since reductions of numbers of covariates to manageable size with the lasso will significantly simplify the analysis, allowing the possibility of an entirely nonparametric approach to survival.

These statistical tools are applicable to all manner of marker expression data. A set of data that can be easily determined, and that is highly informative regarding detection of individuals with clinically significant responsiveness to therapy is provided.

Also provided are databases of signature patterns for responsiveness. Such databases will typically comprise signature patterns of individuals having responsive phenotypes, non-responsive phenotypes, etc., where such profiles are as described above.

Clinical Factors

In some embodiments, one or more clinical factors in a subject can be assessed. In some embodiments, assessment of one or more clinical factors in a subject can be combined with a marker analysis in the subject to identify responder v. non-responder status of the subject.

Various clinical factors are generally known one of ordinary skill in the art to be associated with the disease in question, e.g. MS. In some embodiments, clinical factors known to one of ordinary skill in the art to be associated with the disease, can include age, gender, race, family history, and/or medications. In some embodiments, a clinical factor can include age at onset of disease, duration of therapeutic treatment, and/or the relapse rate of the subject. Other examples of clinical factors are described in the Example section, e.g., Table 2.

Therapeutic Agents

In one embodiment of the invention, a therapeutic agent is provided to a subject with MS based on the patient group the subject is classified into. For example, a subject classified in Groups 1 or 5 (e.g., prognosed as responsive to IFN-β) may continue to be treated with IFN-β, while an individual classified in Groups 3 or 6 (e.g. prognosed as non-responder) may be treated with therapy other than IFN-β, e.g. glatiramer acetate, corticosteroids, etc. as described below. In some embodiments, an individual prognosed as responsive to IFN-β (e.g. Group 1 or Group 5) may also be treated with an alternative therapy in addition to or in replacement of IFN-β. Subjects classified in Groups 2 or 4 may be treated with either IFN-β, an alternative therapy, or any combination thereof.

Treatments for MS include IFN-β (Avonex, Betaseron, Rebif) and Copaxone® (Glatiramer acetate), which reduce relapse rate and to date have only exhibited a modest impact on disease progression. Additional treatments for MS include anti-VLA4 (Tysabri, natalizumab), dimethyl fumarate (Tecfidera®), and teriflunomide (Aubagio®). MS is also treated with immunosuppressive agents including methylprednisolone, other steroids, fingolimod (Gilenya®), methotrexate, cladribine and cyclophosphamide. Treatments may also include those currently in clinical development for MS such as anti-IFN-γ antibody, CTLA4-Ig (e.g., Abetacept), anti-CD20 (e.g., rituximab or ocreluzimab), anti-CD52 antidoby (e.g., alemtuzumab), and other anti-cytokine agents. Treatments can also include a bone marrow stem cell transplant.

In various embodiments the therapeutic agent is a biologic, e.g. a cytokine, antibody, soluble cytokine receptor, anti-sense oligonucleotide, siRNA, etc. Such biologic agents encompass muteins and derivatives of the biological agent, which derivatives can include, for example, fusion proteins, pegylated derivatives, cholesterol conjugated derivatives, and the like as known in the art. Also included are antagonists of cytokines and cytokine receptors, e.g. traps and monoclonal antagonists, e.g. IL-1Ra, IL-1 Trap, sIL-4Ra, etc. Also included are biosimilar or bioequivalent drugs to the active agents set forth herein.

The method also provide for combination therapy, where the combination can provide for additive or synergistic benefits. Combinations of agents can be obtained with a second agent selected from one or more of the general classes of drugs commonly used in the treatment of the disease of interest, for example including corticosteroids and disease modifying drugs, antigen-specific agents, etc. Corticosteroids have a short onset of action, but many disease modifying drugs take several weeks or months to demonstrate a clinical effect. These agents include methotrexate, leflunomide (Arava™), etanercept (Enbrel™) infliximab (Remicade™), adalimumab (Humira™), anakinra (Kineret™), rituximab (Rituxan™), CTLA4-Ig (abatacept), antimalarials, gold salts, sulfasalazine, d-penicillamine, cyclosporin A, cyclophosphamide azathioprine; and the like. Corticosteroids, e.g. prednisone, methylpredisone, prednisolone, solumedrol, etc. have both anti-inflammatory and immunoregulatory activity. They can be given systemically or can be injected locally. Corticosteroids are useful in early disease as temporary adjunctive therapy while waiting for disease modifying agents to exert their effects. Corticosteroids are also useful as chronic adjunctive therapy in patients with severe disease.

In some embodiments of the invention the therapeutic agent is a beta-interferon, including without limitation the currently approved drugs AVONEX™ (IFNβ 1A), BETASERON™ (IFN-β1B); EXTAVIA™ (IFN-β1B), REBIF™ (IFNβ1A), and bioequivalents and derivatives, e.g. pegylated derivatives, thereof. Conditions that can be treated with β-interferons include MS, EAE, etc. Such diseases can also be treated with glatiramer acetate (Copaxone®).

In some embodiments of the invention the therapeutic agent is a cytokine or an antagonist, agonist, mimetic, bioequivalent, or derivative thereof. Cytokines of interest include, without limitation, IL-1β, IL-2; IL-4; IL-5; IL-6; IL-7; IL-8; IL-10; IL-11; IL-12; IL-13; IL-15; IL-17 (including IL-17A, B, C, D, E, F separately and in combination, such as IL-17A/F); IL-18; IL-20; IL-21; IL-23; and IL29.

Antagonists of interleukins which can be soluble receptors, antibodies, small molecule drugs, etc. include, without limitation, anti-IL-1, e.g. canakinumab, anakinra, rilonacept, AMG108, XOMA052; anti-IL-4, AMG317; anti-IL-5, mepolizumab, reslizumab, SCH55700, MEDI-563 (receptor); anti-IL6, siltuximab, tocilizumab (receptor), CNTO 136; anti-IL-8, ABX-IL8; anti-IL-9, MEDI-528; anti-IL-12 and IL-23, ustekinumab, briakinumab; anti-IL-13, CAT-354, QAX576; anti-IL-15, AMG 714; anti-IL-17, AIN457, LY2439821, NI-1401; anti-IL-18, GSK1070806; anti-IL-20, NNC109-0012; anti-IL-22, fezakinumab; anti-IL-23, LY2525623. STA-5326 (also called apilimod) is a small molecule inhibitor of IL-12/23 function. LY2439821 and secukinumab (AIN457) are examples of anti-IL-17 monoclonal antibodies.

Antagonists of cytokines include antagonists of IFN-α (anti-IFNα); IFNβ (anti-IFNβ); IFN-γ (anti-IFN-γ); G-CSF (anti-G-CSF); GM-CSF (anti-GM-CSF); Groα (anti-Groα); etc. Agonists of TNFα (anti TNFα e.g. Enbrel (etanercept), Arcalyst (rilonacept), Amevive (alefacept), find use, for example in the treatment of rheumatic diseases. As used herein, rheumatic diseases can include Ankylosing Spondylitis, Gout, Rheumatoid Arthritis, acute and subacute Bursitis, Kawasaki Syndrome, Relapsing Polychondritis, Bursitis and Tendinitis, Juvenive Idiopathic Arthritis (Juvenile Rheumatoid Arthritis), Sjogren's Syndrome, Cryopyrin-associated Periodic Syndromes, Osteoarthritis, Systemic Sclerosis, Dermatomyositis, Polymyalgia Rheumaticia, Systemic Lupus Erythematous, Epicondylitis, Polymyositis, acute non-specific Tenosynovitis, Fibromyalgia, Psoriatic Arthritis and Vasculitis. Therapies known for rheumatic diseases also include Abatacept (Orencia); Adalimumab (Humira); Anakinra (Kineret); Aspirin (Ecotrin); Auranofin (Ridura); Aurothioglucose (Solganal); Azathioprine (Imuran); Celecoxib (Celebrex); Cyclosporin (Neoral); Etanercept (Enbrel); Gold sodium thiomalate (Myochrysine); Hydroxychloroquine Sulfate (Plaquenil); Infliximab (Remicade); Intravenous Immunoglobulin (Gammagard S/D); Leflunomide (Arava); Methylprednisolone acetate (Depo-Medrol); Methotrexate (Rheumatrex, Trexall); Penicillamine (Cuprimine); Prednisolone (Prednisone (Corticosteroids); Rilonacept (Arcalyst); Rituximab (Rittman); Sulfasalazine (Azulfidine (Azulfidine EN-Tabs); Triamcinolone acetonide (Kenalog); Triamcinolone diacetate (Aristospan); Diclofenac (Voltaren (Cataflam (Arthrotec (combined with misoprostol)); Diflunisal (Dolobid); Etodolac (Lodine (Lodine XL); Fenoprofen (Nalfon (Nalfon 200); Flurbiprofen (Ansaid); Ibuprofen (Motrin, Tab-Profen, Vicoprofen, combined with hydrocodone) (Combunox, combined with oxycodone); Ibuprofen (Children's Advil); Indomethacin (Indocin, Indocin SR, Indo-Lemmon); Ketoprofen (Oruvail, Orudis); Meloxicam (Mobic); Nabumetone (Relafen); Naproxen (Naprosyn, Anaprox, Anaprox DS, EC-Naprosyn, Naprelan); Oxaprozin (Daypro); Piroxicam (Feldene); Sulindac (Clinoril); Tolmetin (Tolectin, Tolectin DS, Tolectin 600). Agents that find use in the treatment of chronic hepatitis include, for example, ALFERONN™ INJECTION (IFN-αN3); INFERGEN™ (IFN-αCON-1); INTRON A™ (IFN-α2B); PEGASYS™ (PEG IFN-α2A); PEGINTERFERON™ (PEGIFN-α2A; RIBAVIRIN); PEGINTRON™ (PEGIFN-α2B); ROFERON A™ (IFN-α2A).

Agents that have been found useful in treating inflammatory diseases also include statins, e.g. pravastatin, simvastatin, lovastatin, fluvastatin, atorvistatin, pitavastatin, rosuvastatin, etc.

Monoclonal antibodies in use include, without limitation, ACTEMRA™ (tocilizumab); ARZERRA™ (ofatumumab); BEXXAR™ (tositumomab; $^{131}$I tositumomab); CAMPATH™ (alemtuzumab); CIMZIA™ (certolizumab pegol); HUMIRA™ (adalimumab); ILARIS™ (canakinumab); PROLIA™ (denosumab); REMICADE™ (infliximab); RITUXAN™ (rituximab); SIMPONI™ (golimumab); SIMULECT™ (basiliximab); STELARA™ (ustekinumab); TYSABRI™ (natalizumab); XGEVA™ (denosumab); XOLAIR™ (omalizumab); ZENAPAX™ (daclizumab). Monoclonal antibodies specific for amyloid include LY2062430 (solanezumab), PF-04360365, MABT5102A, bapineuzumab, gantenerumab.

Other therapeutic agents of interest include lenalidomide (Revlimid); fingolimod (Gilenya); teriflunomide; cladribine; and BG-12 (Panaclar, BG-00012, FAG-201); JAK inhibitors and Syk inhibitors, which include without limitation the JAK-3 inhibitor tasocitinib (CP-690,550); Syk inhibitor fostamatinib (R788) etc.

Interferon beta-1a is a drug in the interferon family used to treat multiple sclerosis (MS). It is produced by mammalian cells while Interferon beta-1b is produced in modified *E. coli*. Interferons have been shown to have about a 18-38% reduction in the rate of MS relapses, and to slow the progression of disability in MS patients. Commercially available products include Avonex (Biogen Idec); Rebif (EMD Serono); and CinnoVex (CinnaGen). Closely related is Interferon beta-1b, which is marketed in the US as Betaseron, or Extavia. IFN-β find use in the treatment of patients classified by the methods of the invention as responsive to IFN-β.

Copaxone®, manufactured by Teva Marion Partners, is the brand name for a synthetic chemical used to modify the course of multiple sclerosis. The generic name of Copaxone® is Glatiramer Acetate which is often shortened to GA. In early trials of the drug, it was known as Copolymer-1 and Cop-1. Copaxone® is a random chain of amino acids—Glutamic acid, Lysine, Alanine and Tyrosine (hence GLATiramer). It is synthesized in solution from these amino acids a ratio of approximately 5 parts Alanine to 3 of Lysine, 1.5 of Glutamic acid and 1 of Tyrosine using N-carboxyamino acid anhydrides. Copaxone® has been shown in clinical trials to reduce the average relapse rate in people with the relapsing-remitting (RRMS) form of the disease. Copaxone® has also been shown to limit the formation of new MS-related lesions in the central nervous system and to reduce brain atrophy. Copaxone® finds use in the treatment of patients classified by the methods of the invention as unresponsive to IFN-β.

Simvastatin, the lipid-lowering drug first marketed as Zocor, has been investigated for use in multiple sclerosis, and shown to inhibit Th17 cell differentiation in patients with relapsing-remitting multiple sclerosis. Experiments suggest that simvastatin alters CD45RA+ cells undergoing Th17 differentiation. Simvastatin and other statins find use in the treatment of patients classified by the methods of the invention as unresponsive to IFN-β.

The methods of treatment (prophylactic and/or therapeutic) can also utilize a therapeutic agent. The therapeutic agent(s) are administered in a therapeutically effective amount (i.e., an amount that is sufficient for "treatment," as described above). The amount which will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

Patients categorized as non-responders can be treated with, for example, natalizumab, dimethyl fumarate, fingolimod, teriflunomide, statins, methylprednisolone, methotrexate, cladribine, cyclophosphamide, anti-IFN γ antibody, CTLA4-Ig, anti-CD20 antibody (rituximab or ocreluzimab), anti-CD52 antibody (alemtuzumab), IL-17 inhibitor, IL-23 inhibitor, and bone marrow stem cell transplantation, etc. as an alternative to IFN-β. Inhibitors include neutralizing antibodies specific for at least IL-17F or IL-23 protein, soluble IL-17F or IL-23 receptor; inactive forms of IL-17F or IL-23; and the like.

Clinical trials describing various therapeutic agents, appropriate dosage regimens, and the like for MS are as follows: O'Connor et al., A Phase II study of the safety and efficacy of teriflunomide in multiple sclerosis with relapses, Neurology, 2006 Mar. 28; 66(6):894-900; Kappos et al, A placebo-controlled trial of oral fingolimod in relapsing multiple sclerosis, N Engl J Med. 2010 Feb. 4; 362(5):387-401. Epub 2010 Jan. 20; Cohen et al, Oral fingolimod or intramuscular interferon for relapsing multiple sclerosis, N Engl J Med. 2010 Feb. 4; 362(5):402-15. Epub 2010 Jan. 20. All of these references are herein incorporated by reference.

In some embodiments the therapeutic agents are antibodies. The term "antibody" is used in the broadest sense and specifically covers monoclonal antibodies (including full length monoclonal antibodies), polyclonal antibodies, multispecific antibodies (e.g., bispecific antibodies), and antibody fragments that are antigen-binding so long as they exhibit the desired biological activity, e.g., an antibody or an antigen-binding fragment thereof "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

Antigen specific therapeutic methods include administration of an antigen or epitope specific therapeutic agent. One method to induce immune tolerance is tolerizing DNA vaccines (Garren et al. (2001) Immunity, 15:15-22; Robinson et al. (2003) Nature Biotechnology 21:1033-9). Tolerizing DNA vaccines are DNA plasmids containing the regulatory regions necessary for expression of the encoded cDNA in mammalian cells, and would be engineered to contain cDNA sequence encoding all or a portion of a targeted antigen in order to induce immune tolerance to the encoded epitopes. To enhance the ability of such plasmids to induce immune tolerance, the immunostimulatory CpG sequences (Krieg et al. (1998) Trends Microbiol. 6:23-27) can be reduced in number or completely removed from the plasmid vector. Additionally, immunoinhibitory GpG sequences can be added to the vector (see Ho et al. (2005) J. Immunology, 175:6226-34). Tolerizing DNA plasmids are delivered intramuscularly to induce immune tolerance to an antigen, thereby reducing T cell and autoantibody responses to reduce autoimmune destruction of the myelin sheath.

As an alternative, or in addition to DNA tolerization, specific peptides, altered peptides, or proteins can be administered therapeutically to induce antigen-specific tolerance to treat autoimmunity. Native peptides targeted by the autoimmune response can be delivered to induce antigen-specific tolerance (Science 258:1491-4). Native peptides have been delivered intravenously to induce immune tolerance (J Neurol Sci. 152:31-8). Delivery of peptides that are altered from the native peptide, is also known in the art. Alteration of native peptides with selective changes of crucial residues (altered peptide ligands or "APL") can induce unresponsiveness or change the responsiveness of antigen-specific autoreactive T cells. In another embodiment, whole protein antigens targeted by the autoimmune response can be delivered to restore immune tolerance to treat autoimmunity (Science 263:1139).

Compositions and Administration of Therapeutic Agents

Active ingredients in pharmaceutical compositions formulated for the treatment of various disorders are as described above. The active ingredient is present in a therapeutically effective amount, i.e., an amount sufficient when administered to substantially modulate the effect of the targeted protein or polypeptide to treat a disease or medical condition mediated thereby. The compositions can also include various other agents to enhance delivery and efficacy, e.g. to enhance delivery and stability of the active ingredients.

Thus, for example, the compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

When the pharmaceutical composition includes a polypeptide as the active ingredient, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lies within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, or intracranial method.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that can be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which are composed of the packaged active ingredient with a suppository base. Suitable suppository bases include natural or synthetic triglycerides or paraffin hydrocarbons. In addition, it is also possible to use gelatin rectal capsules, which are composed of a combination of the packaged active ingredient with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are preferably sterile. To the extent that a given compound must be synthesized prior to use, the resulting product is preferably substantially free of any potentially toxic agents, such as any endotoxins, which can be present during the synthesis or purification process. Compositions for parental administration are also preferably sterile, substantially isotonic and made under GMP conditions.

The compositions can be administered in a single dose, or in multiple doses, usually multiple doses over a period of time, e.g. daily, every-other day, weekly, semi-weekly, monthly etc. for a period of time sufficient to reduce severity of the inflammatory disease, which can comprise 1, 2, 3, 4, 6, 10, or more doses.

Determining a therapeutically or prophylactically effective amount an agent can be done based on animal data using routine computational methods. In one embodiment, the therapeutically or prophylactically effective amount contains between about 0.1 mg and about 1 g of nucleic acid or protein, as applicable. In another embodiment, the effective amount contains between about 1 mg and about 100 mg of protein, as applicable. In a further embodiment, the effective amount contains between about 10 mg and about 50 mg of the nucleic acid or protein, as applicable. The effective dose will depend at least in part on the route of administration. The agents can be administered orally, in an aerosol spray; by injection, e.g. intramuscular, subcutaneous, intraperitoneal, intravenous, etc. In some embodiments, administration by other than i.v. can be preferred. The dose can be from about 0.1 µg/kg patient weight; about 1 µg/kg; about 10 µg/kg; to about 100 µg/kg.

The compositions are administered in a pharmaceutically acceptable excipient. The term "pharmaceutically acceptable" refers to an excipient acceptable for use in the pharmaceutical and veterinary arts, which is not toxic or otherwise inacceptable. The concentration of compositions of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

Treating, treatment, or therapy of a disease or disorder shall mean slowing, stopping or reversing the disease's progression by administration of treatment according to the present invention. In the preferred embodiment, treating a disease means reversing the disease's progression, ideally to the point of eliminating the disease itself. As used herein, ameliorating a disease and treating a disease are equivalent. Preventing, prophylaxis or prevention of a disease or disorder as used in the context of this invention refers to the administration of a composition to prevent the occurrence or onset of a disease or disorder or some or all of the symptoms of a disease or disorder or to lessen the likelihood of the onset of a disease or disorder.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

Computer Implementation

The methods of the invention, including the methods of prognosing responsiveness of a subject with multiple sclerosis to treatment with interferon β (IFN-β), are, in some embodiments, performed on a computer.

For example, the biomarker analysis (e.g. statistical analysis) and database storage can be implemented in hardware or software, or a combination of both. In one embodiment of the invention, a machine-readable storage medium is provided, the medium comprising a data storage material encoded with machine readable data which, when using a machine programmed with instructions for using said data, is capable of displaying any of the datasets and data comparisons of this invention. Such data can be used for a variety of purposes, such as patient monitoring, treatment considerations, and the like. The invention can be implemented in computer programs executing on programmable computers, comprising a processor, a data storage system (including volatile and non-volatile memory and/or storage elements), a graphics adapter, a pointing device, a network adapter, at least one input device, and at least one output device. A display is coupled to the graphics adapter. Program code is applied to input data to perform the functions described above and generate output information. The output information is applied to one or more output devices, in known fashion. The computer can be, for example, a personal computer, microcomputer, or workstation of conventional design.

Each program can be implemented in a high level procedural or object oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

In various embodiments, each of the subject groups (e.g. Group 1, Group 2, Group 3, Group 4, Group 5, and Group 6) is previously determined using a computer. For example, the subject groups can be determined using hierarchical clustering analysis of biomarkers derived from samples previously obtained from patients such as MS patients. In various aspects, the hierarchical clustering analysis is complete linkage clustering. In some aspects, the hierarchical clustering analysis is single linkage clustering, average linkage clustering, centroid linkage clustering, minimum energy clustering, and Ward's method.

The hierarchical clustering analysis of biomarkers can be conducted using executable code that is stored on a computer. In various aspects, the executable code is downloadable open source code such as Cluster 3.0 (accessible at http://bonsai.hgc.jp/~mdehoon/softwafe/cluster/software.htm#ctv).

The baseline serum marker levels of individuals can be provided to the computer to cluster the individuals. Further details in regards to the clustering analysis can be found at Eisen et al. PNAS. 1998, 95(25):14863-14868. Briefly, for N individuals, a N×N similarity matrix may be constructed. Each entry includes a similarity score representing the similarity in baseline serum biomarker expression levels between a first individual and a second individual from the N different individuals. The entry with the highest similarity score is combined to form a node of a dendrogram. The matrix is updated with this newly formed node and the process is repeated N-1 times to repeatedly develop additional nodes of the dendrogram. Therefore, the N individuals are clustered into a single element.

Kits

Also disclosed herein are kits for prognosing responsiveness of a subject with multiple sclerosis to treatment with interferon β (IFN-β). Such kits can include reagents for detecting expression levels of one or markers and instructions for classifying a MS patient in one of six distinct subject groups based on the expression levels.

The detection reagents can be provided as part of a kit. Thus, the invention further provides kits for detecting the presence of a panel of specific markers of interest in a biological sample. A kit can comprise a set of reagents for generating a dataset via at least one protein detection assay that is associated with a sample from the subject comprising data representing biomarker levels corresponding to two, three, or more of IL-8, CXCL1/Groα, IL-43, IL-1RA, CCL2/MCP1, IFN-β, IL-17F, CD40L, G-CSF, CXCL10/IP10, and IL-6; and instructions for classifying the subject in at least one of group 1, group 2, group 3, group 4, group 5, and group 6. In certain aspects, the reagents comprise one or more antibodies that bind to one or more of the biomarkers, optionally wherein the antibodies are monoclonal antibodies or polyclonal antibodies. The reagents can include reagents for performing ELISA including buffers and detection agents.

A kit can include instructions for use of a set of reagents. For example, a kit can include instructions for performing at least one protein detection assay such as an immunoassay, a protein-binding assay, an antibody-based assay, an antigen-binding protein-based assay, a protein-based array, an enzyme-linked immunosorbent assay (ELISA), flow cytometry, a protein array, a blot, a Western blot, nephelometry, turbidimetry, chromatography, mass spectrometry, enzymatic activity, and an immunoassays selected from RIA, immunofluorescence, immunochemiluminescence, immunoelectrochemiluminescence, immunoelectrophoretic, a competitive immunoassay, amd immunoprecipitation.

In addition to the above components, the subject kits will further include instructions for practicing the subject methods. These instructions can be present in the subject kits in a variety of forms, one or more of which can be present in the kit. One form in which these instructions can be present is as printed information on a suitable medium or substrate, e.g., a piece or pieces of paper on which the information is printed, in the packaging of the kit, in a package insert, etc. Yet another means would be a computer readable medium, e.g., diskette, CD, hard-drive, network data storage, etc., on which the information has been recorded. Yet another means that can be present is a website address which can be used via the internet to access the information at a removed site. Any convenient means can be present in the kits.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications and patent applications cited in this specification are herein incorporated by reference as if each individual publication or patent application were specifically and individually indicated to be incorporated by reference. Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and Clon-Tech.

The invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. All such modifications are intended to be included within the scope of the appended claims.

Example 1: Cytokine Profiles Demonstrate Heterogeneity of Interferonβ Response in Patients with Multiple Sclerosis Multiple sclerosis (e.g. RRMS, PPMS, and SPMS) is a highly heterogeneous disease with an unpredictable clinical course and a wide variation in treatment response to first-line therapies, including interferon (IFN)-β. Identification of biomarkers predictive of treatment response in MS patients would contribute to optimization of care. Here, hierarchical clustering analysis was used to assess cytokine profiles in patients with MS before the initiation of IFN-β therapy (baseline) and three months while on therapy. Baseline cytokine profiles clustered patients into six distinct subsets. These MS subsets differed significantly in their clinical and biological response to IFN-β therapy. Two subsets were associated with patients that responded poorly to therapy. Two other subsets that were associated with patients that responded well to therapy, showing significant reduction in relapse rates and an arrest in progression of disability. Each of these subsets had differential changes in cytokine levels after 3 months of IFN-β treatment and these effects were associated with treatment response. There is heterogeneity in the immunological pathways in the RRMS population, which correlates with treatment response and prognosis.

In this study, 51 serum cytokines and chemokines from MS patients were measured before the initiation of therapy (baseline) and three months while on therapy to assess the utility of these analytes to predict treatment response. Three approaches were used for analysis of the cytokines as biomarkers. The first and second approaches compare cytokines at baseline and 3 months after treatment in responders and non-responders defined by relapse rates and changes of Expanded Disability Status Scale (EDSS) score, respectively. The third approach uses the variability of baseline cytokine levels for hierarchical clustering of MS patients into subsets, and then subsequently compares and correlates the clinical and biological outcomes to IFN-β treatment between these subsets.

Results

Comparison at Baseline and 3 Months of Cytokines of Responders Versus Non-Responders Defined by Relapses.

Responders were defined as patients that did not relapse two years after initiating IFN-β therapy. In this patient cohort, 67 of 157 (42.7%) of patients were defined as non-responders. The baseline clinical and demographic features of responders and non-responders showed no statistically significant differences in disease type, the age of onset, disease duration before initiating therapy, sex, EDSS, or drug type (Table 2). Non-responders had significantly greater relapse rates prior to treatment compared to responders demonstrating that as a population the non-responders have increased disease activity (Table 2).

Baseline serum cytokine levels were then compared between responders and non-responders. The concentrations of cytokines were highly variable in this cohort and did not have a normal Gaussian distribution. Therefore, cytokine values were $log_2$-transformed for comparison between responders and non-responders using logistic regression. Of all 51 cytokines measured at baseline, only IL-1β was significantly different between responders and non-responders with an odds ratio (OR) of 1.45 (95% CI=1.09-1.93, Table 3). Serum concentration of IL-1β was significantly higher in non-responders compared to responders (FIG. 1A). This result confirms a recent study that reported IL-1β was elevated in IFN-β non-responders.

Figure 6:
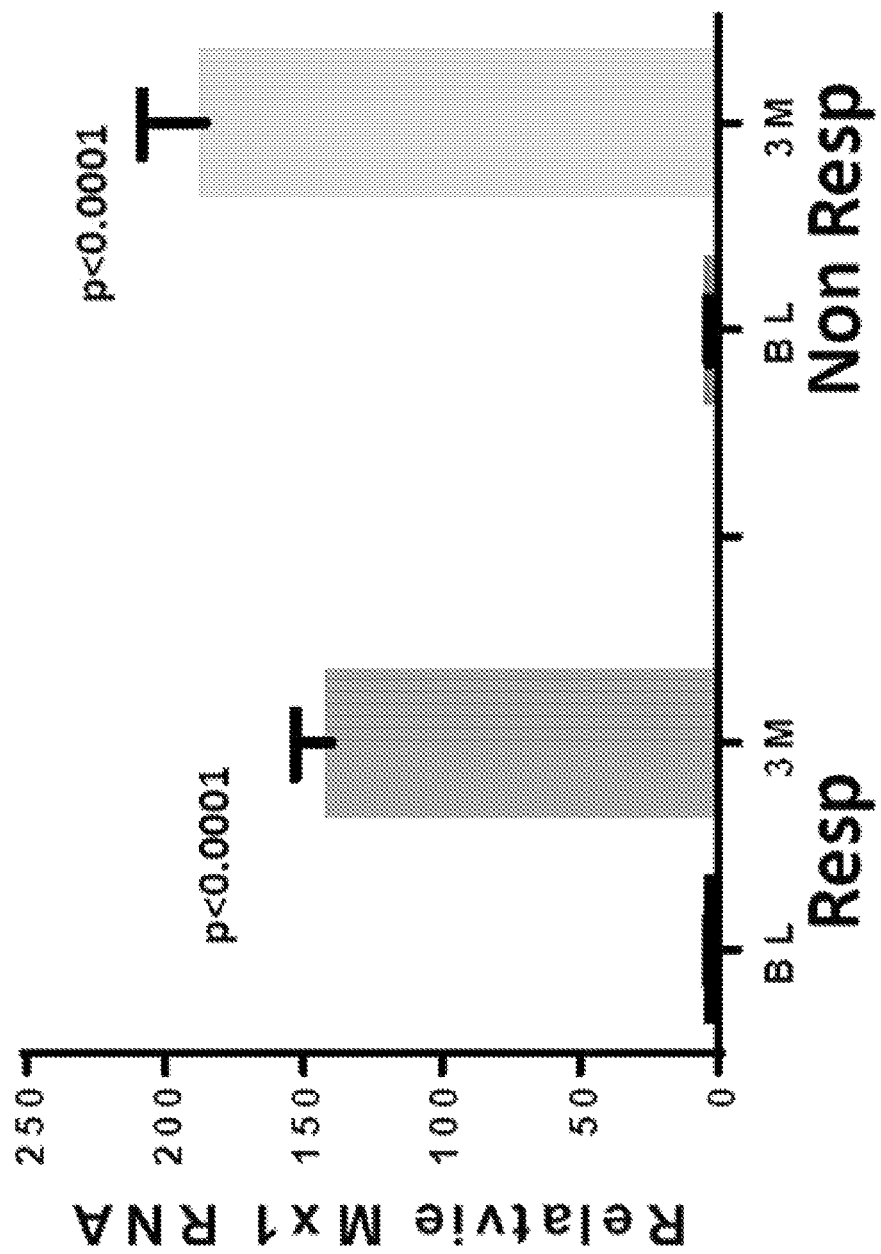
FIG. 6 shows changes in MxA transcription levels from baseline (BL) to 3 months (3M) in responders and non-responders determined based on relapse rate.

Next, changes in cytokine levels at three months (3M) versus baseline (BL) in responders and non-responders were compared. Furthermore, concentrations of myxovirus protein A (MxA), which is specifically induced by type I IFNs and well established as surrogate for IFN-β bioavailability was determined. At 3M, both responders and non-responders had significantly elevated levels of CXCL10/IP10, CCL2/MCP1 and MxA (FIG. 1B, C and FIG. 6). The expression of MxA and of the cytokines CXCL10 and CCL2 demonstrates that IFN-β treatment is biologically active in both responder and non-responders. Additionally, both responders and non-responders had increases in IL-1α, VCAM and IFN-β (Table 4). Previous reports have shown that TNF-related apoptosis inducing ligand (TRAIL) is a potential response biomarker for IFN-β treatment. In this study, soluble TRAIL (sTRAIL) was significantly elevated by IFN-β treatment in responders but not in the non-responders confirming these findings (FIG. 1D). Additionally, G-CSF, TGFβ, ICAM, IL-12p40, MIP1β, CD40L, IL-1RA and MIP1a were elevated in the responders but not the non-responders (Table 4). Finally, IL-8 was statistically decreased while IFN-α and TNFβ were significantly increased after 3 months of IFN-β treatment in the non-responders but not the responders (FIG. 1E and Supplemental Table 3). It is also of note that no difference was observed in the development of neutralizing antibodies (NAbs) to IFN-β within two years between responders and non-responders (9 of 90 and 7 of 67, respectively). However, levels of CXCL10 at 3M were significantly lower in patients that had developed NAbs within two years (NAb$^{pos}$=147.1 pg/ml SD±29.3 vs NAb$^{neg}$=262.7 pg/ml SD±16.1, p=0.0082) thus confirming that NAb development inhibits the biological response to therapy.

Comparison at Baseline and 3 Months of Cytokines of Responders Versus Non-Responders Defined by EDSS For this analysis, a non-responder was defined to have an increase of 1 EDSS point from baseline to 2 years after initiation of therapy. In this patient cohort, baseline and 2 year EDSS data was obtained from 153 patients. Using this outcome, 39 of 153 (24.8%) of patients were defined as non-responders. The baseline clinical and demographic features of EDSS responders and non-responders showed no statistically significant differences in disease type, the age of onset, disease duration before initiating therapy, sex, EDSS, or drug type (Table 5). Responders had significantly greater EDSS score at baseline compared to non-responders (Table 5).

Next, baseline serum cytokine levels in the EDSS responders and non-responders were compared. Of the 51 cytokines, MIG was significantly different between responders and non-responders with an OR of 0.81 (95% CI=0.66-1, Table 6). Serum concentration of MIG were statistically higher in the responders compared to the non-responders (FIG. 1F).

Figure 7:
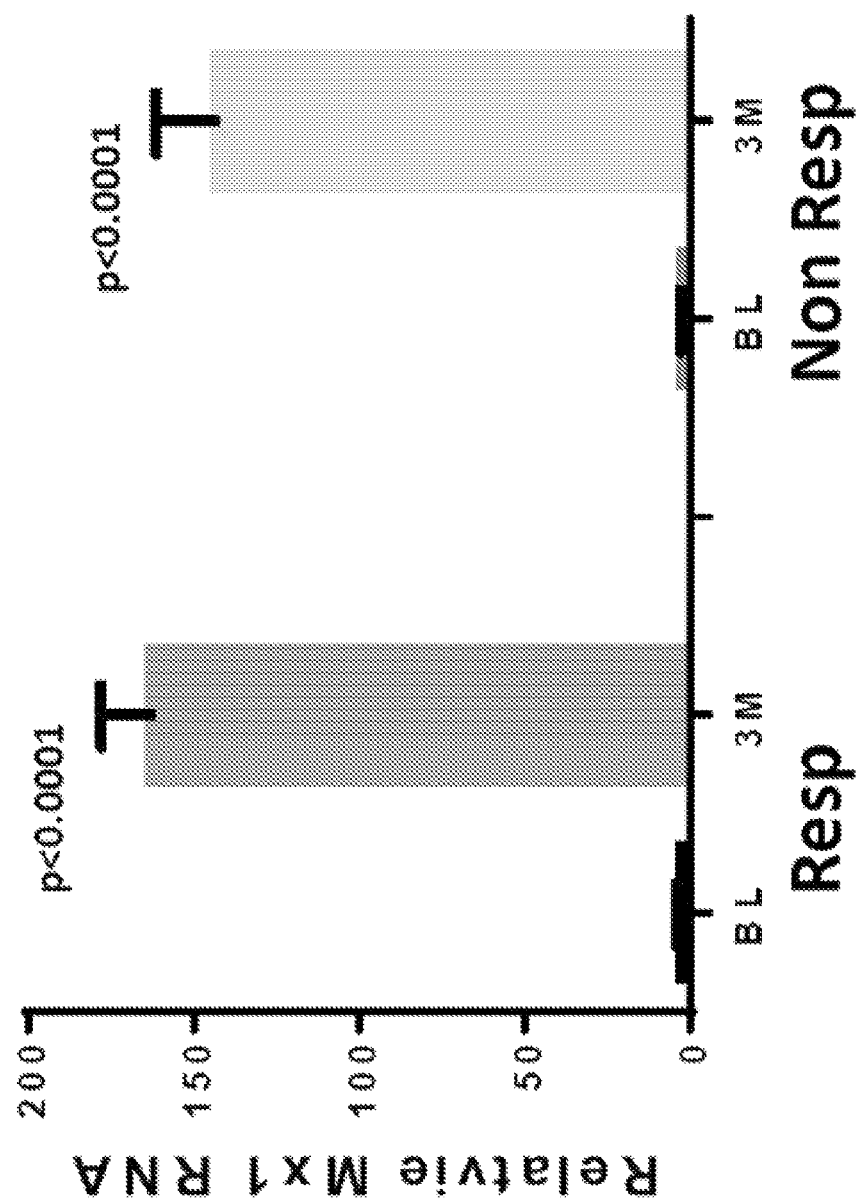
FIG. 7 shows changes in MxA transcription levels from baseline (BL) to 3 months (3M) in responders and non-responders determined based on EDSS score.

Changes in cytokine and MxA transcription levels (3M versus BL) in responders and non-responders were also compared. Similar to the relapse response, both responders and non-responders had significant elevation of MxA, CXCL10/IP10 and CCL2/MCP1 at 3M (FIG. 1G, H and FIG. 7), however sTRAIL did not significantly change in either EDSS responders or non-responders (FIG. 1I). Additionally, IL-8, Plasminogen Activator Inhibitor-1 (PAD, CXCL5/ENA78 and Hepatocyte growth factor (HGF) were all significantly decreased at 3M in the responders but not the non-responders (FIG. 1J and Table 7). CD40L, IL-17A and Nerve Growth Factor (NGF) were significantly increased at 3M in the responders but not the non-responders (Table 7). Finally, VCAM was significantly increased at 3M in the non-responders but not the responders (Table 7).

Baseline Cytokine Profiles Cluster RRMS into Six Distinct Groups

Figure 8:
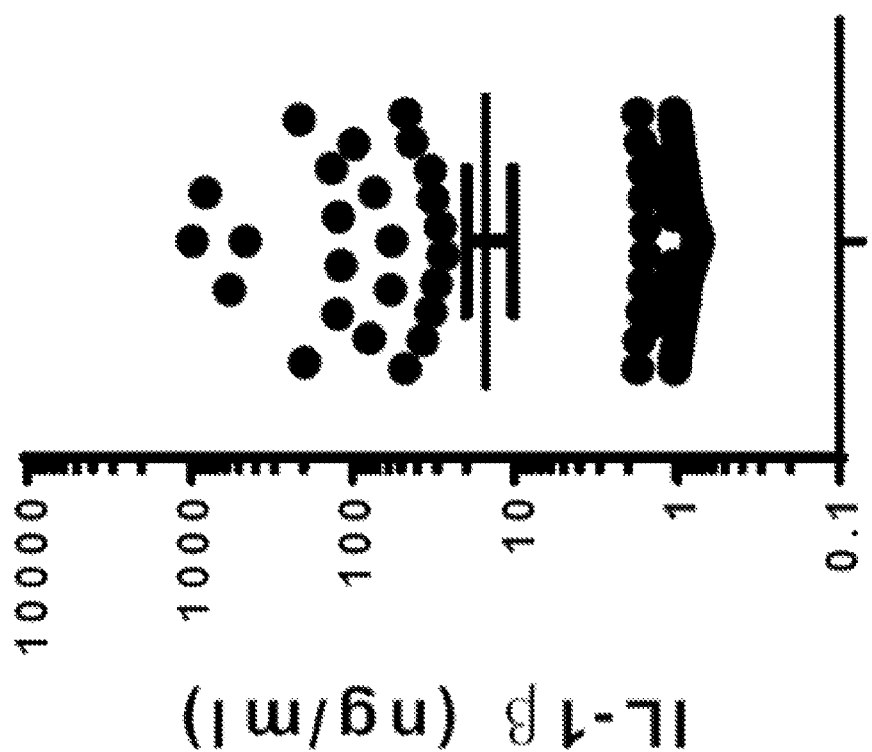
FIG. 8 illustrates the non-Gaussian distribution of IL-1β concentrations in all samples derived from MS patients.

Many cytokines including IL-1β do not have a normal Gaussian distribution across the population (FIG. 8). This suggests that there is immunological heterogeneity in RRMS, thus, cytokines that have the most variability in the population were selected for clinically meaningful stratification of MS patients. In order to select the most variable serum cytokines, the coefficient of variation (CV) of each cytokine from all samples (Table 8) was computed. Cytokines with a CV greater than 100% were selected for hierarchical clustering analysis based on the patients' baseline serum concentrations.

Figure 9:
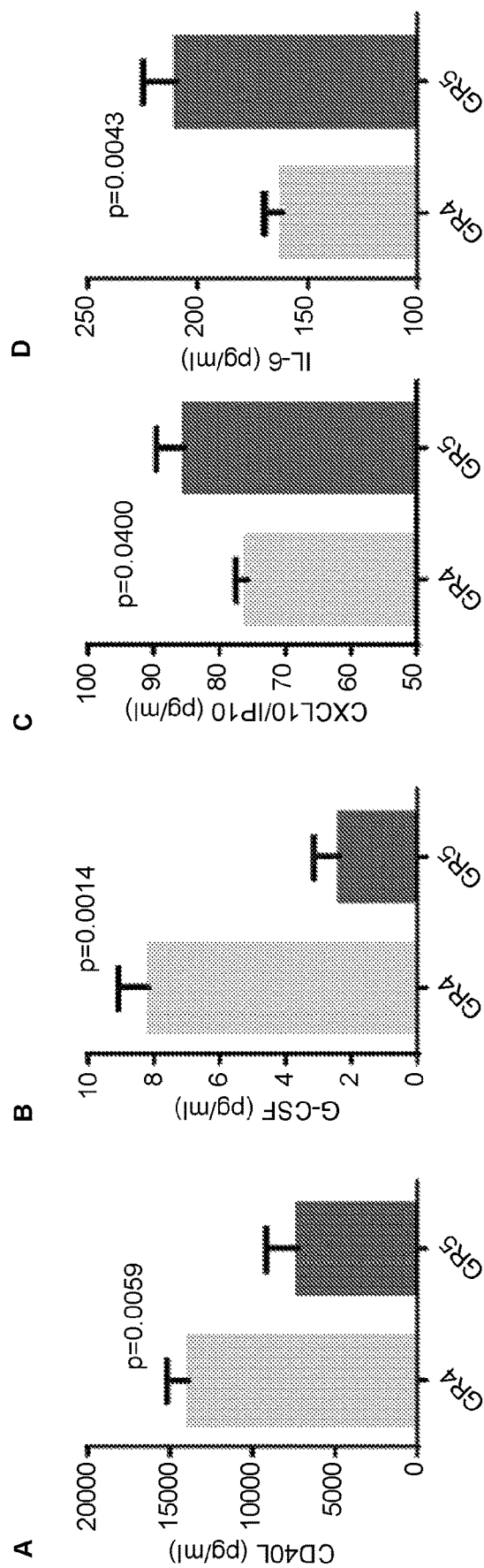
FIG. 9A-9D illustrates cytokine levels of (A) CD40L, (B) G-CSF, (C) CXCL10/IP10, and (D) IL-6 in patients in Group 4 vs patients in Group 5.

As shown in FIG. 2A, clustering baseline cytokines split the RRMS patients into 6 distinct groups. Groups 1, 2, 3 and 6 all have distinct profiles that distinguished them from the rest of the population. Group 3 had statistically higher concentrations of IL-8, CXCL1/Gro-α, IL-1β, IL-1RA and CCL2/MCP1 compared to all other groups (FIG. 2B-F). Group 6 had statistically higher levels of IFN-β and IL-17F compared to all other groups (FIG. 2G-H). Cytokine levels in Group 2 were all low compared to the rest of the groups (FIG. 2A). Patients in Group 1 also had low levels of most cytokines except for CD40L, which distinguished them from Group 2 (FIGS. 2A and I). The cytokine differences that distinguished Groups 4 from 5 were found to be more subtle. Group 4 had higher levels of G-CSF and CD40L compared to Group 5 and conversely Group 5 had higher levels of CXCL10 and IL-6 compared to Group 4 (FIG. 9).

Figure 10:
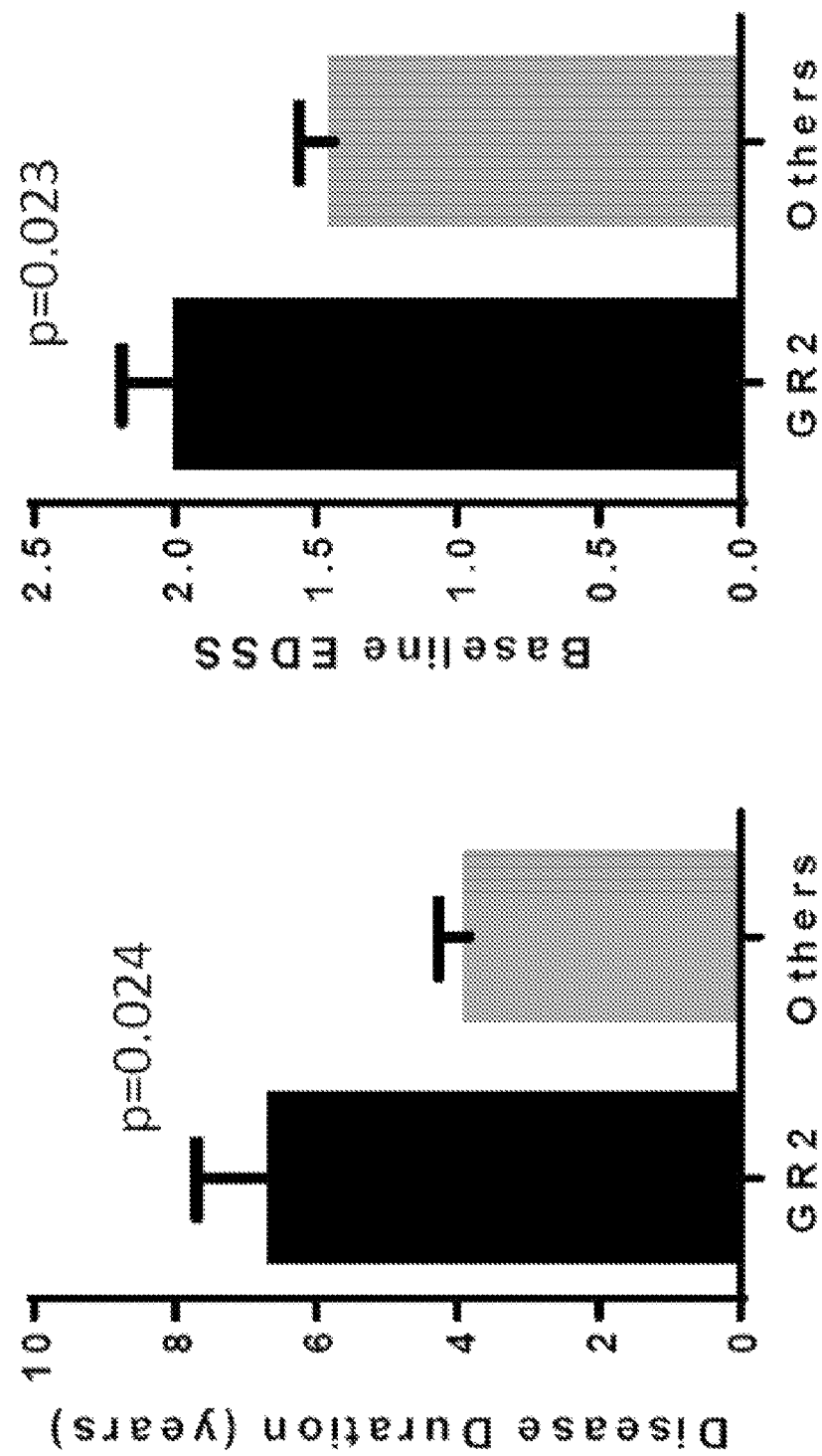
FIG. 10 illustrates disease duration and baseline EDSS score in patients in Group 2 compared to patients in the other groups.

Next, the baseline clinical and demographics features of these 6 groups of RRMS patients was assessed. No significant differences were observed regarding disease type, age, disease duration, sex, baseline EDSS, baseline relapse rates and type of IFN-β treatment given across all groups (Table 9). However, when comparing Group 2 to all other patients, Group 2 had statistically greater duration of disease and greater EDSS before starting therapy (FIG. 10). This difference is of note because Group 2 also had the lowest concentrations of all cytokines.

Differential Clinical Outcome to IFN-β Treatment in the 6 Clustered Groups

Treatment efficacy can be monitored by evaluating the number of clinically defined relapses or by progression in disability (determined by the EDSS score). Both parameters were assessed in the 6 RRMS groups. First, the change in relapse rates two years prior to and two years post initiation of therapy was compared. Groups 1, 2, 4 and 5 all had statistically significant decreases in relapse rates while on IFN-β therapy, whereas there were no statistically significant changes in relapse rates in Group 3 and 6 (FIG. 3A). Additionally, Groups 1 and 5 had a low percentage of patients who had relapses while on IFN-β therapy compared to other groups (Table 1). In contrast, Group 3 and 6 had high percentages patients who had relapses while on IFN-β therapy compared to other patients (Table 1).

Next, the disability progression by comparing the EDSS score from baseline to that after 2 years on interferon therapy was assessed. Group 2 and Group 6 had significant increases in EDSS; Groups 3 and 4 had trends suggesting increased EDSS but did not reach statistical significance; and Groups 2 and 5 showed no progression of EDSS after initiation of IFN-β therapy (FIG. 3B). Taking both relapse rates and EDSS into account, these data suggest that Groups 1 and 5 represent a patient population that is likely to respond to IFN-β therapy, whereas Groups 3 and 6 represent patients that are likely to be non-responders. It is also of interest that the patients in Group 2, which had low baseline cytokine levels and greater duration of disease, had increased EDSS while having decreased relapse rates.

No statistical differences was observed in the frequency of patients who had switched off IFN-β therapy by 2 years post initiation of therapy in the patient groups (Table 10). Additionally, no statistically significant differences in the frequency of patients who developed neutralizing antibodies to IFN-β (Table 10) was observed.

Assessing Baseline IL-7, IL-17F and IL-17A in Extreme MS Phenotypes

In a previous study on baseline serum samples of 26 MS patients, responders and non-responders were selected for two clinical responses to IFN-β therapy based on the number of relapses and the number of times steroids used over two years after initiation of therapy. Levels of IL-7 and IL-17F were inversely correlated and that patients with high levels of IL-17F were non-responders and patients with elevated IL-7 were responders.

Figure 2:
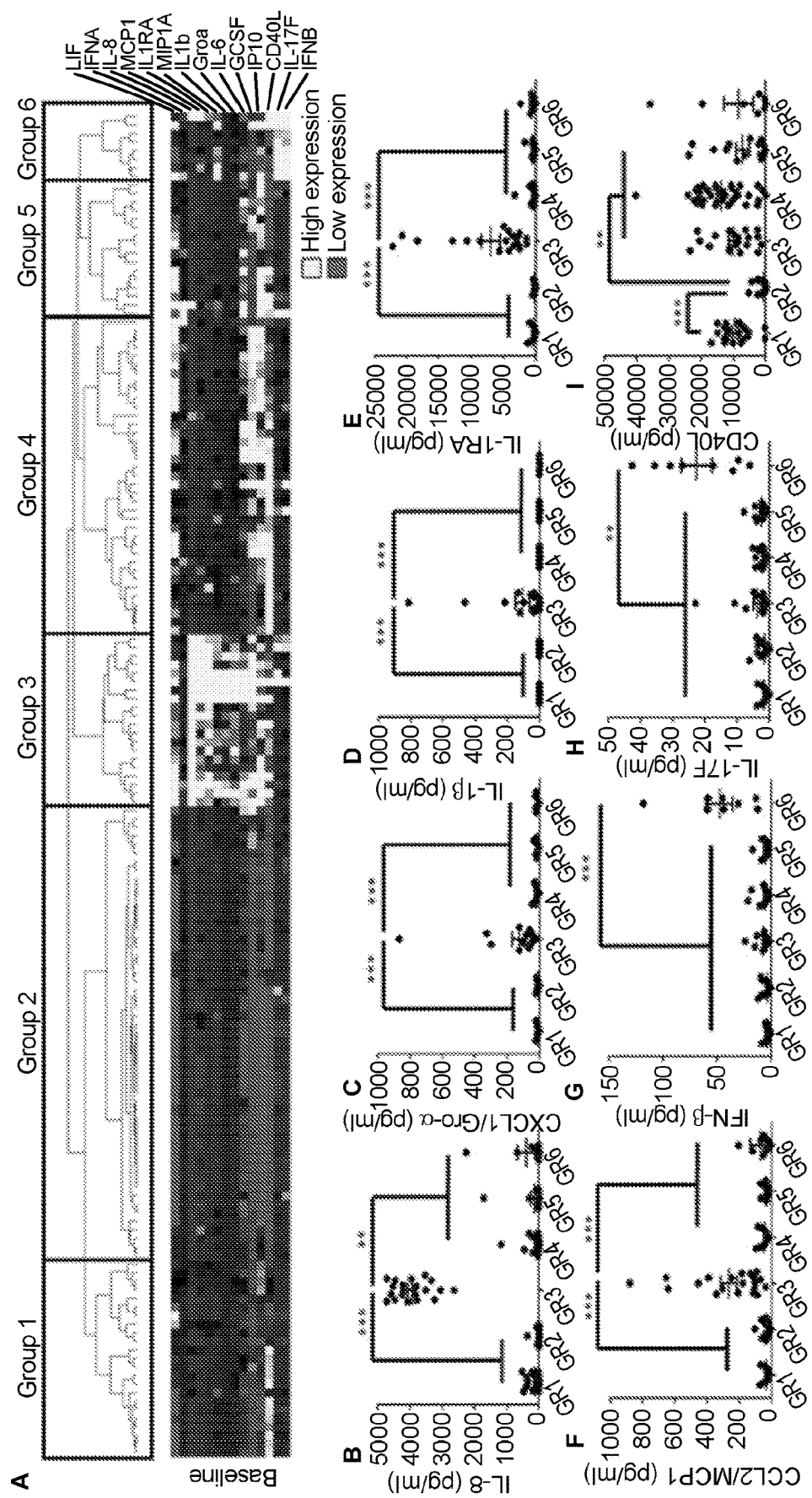
FIG. 2A depicts the cluster analysis of cytokines into 6 distinct subject groups. Heat map depicts relative levels of cytokines and hierarchical clustering of individual patients.
FIG. 2B-2I depict baseline concentrations of (B) IL-8, (C) CXCL1/Gro-α, (D) IL-1β, (E) IL-1RA, (F) CCL2/MCP1, (G) IFN-β, (H) IL-17F and (I) CD40L in the 6 distinct subject groups.
Figure 3:
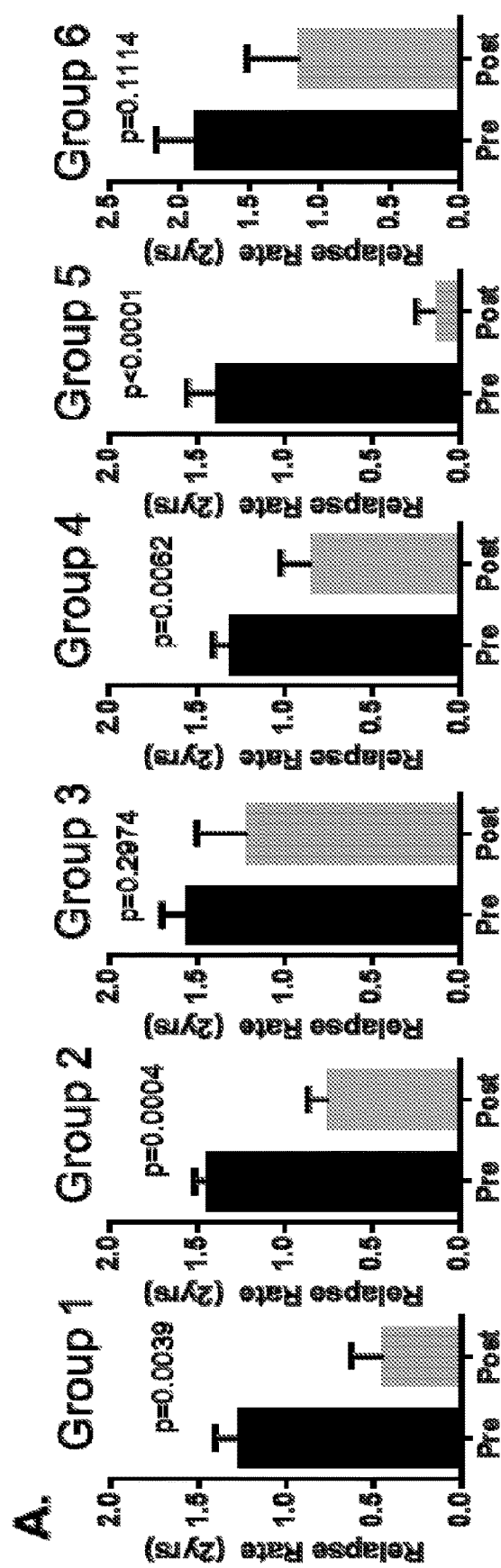
FIG. 3A-3B depict clinical response of patients to IFN-β treatment in the 6 subject groups defined by baseline cytokine profiles. Clinical response is determined based on (A) relapse rate and (B) EDSS score.
Figure 3:
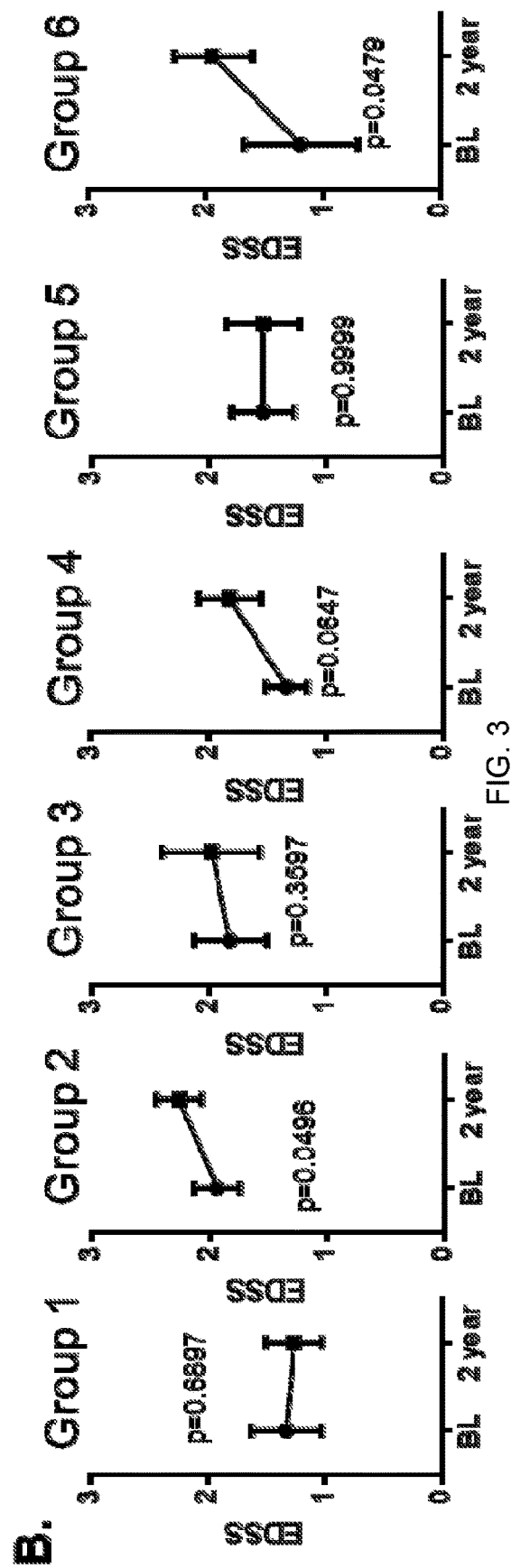
Figure 4:
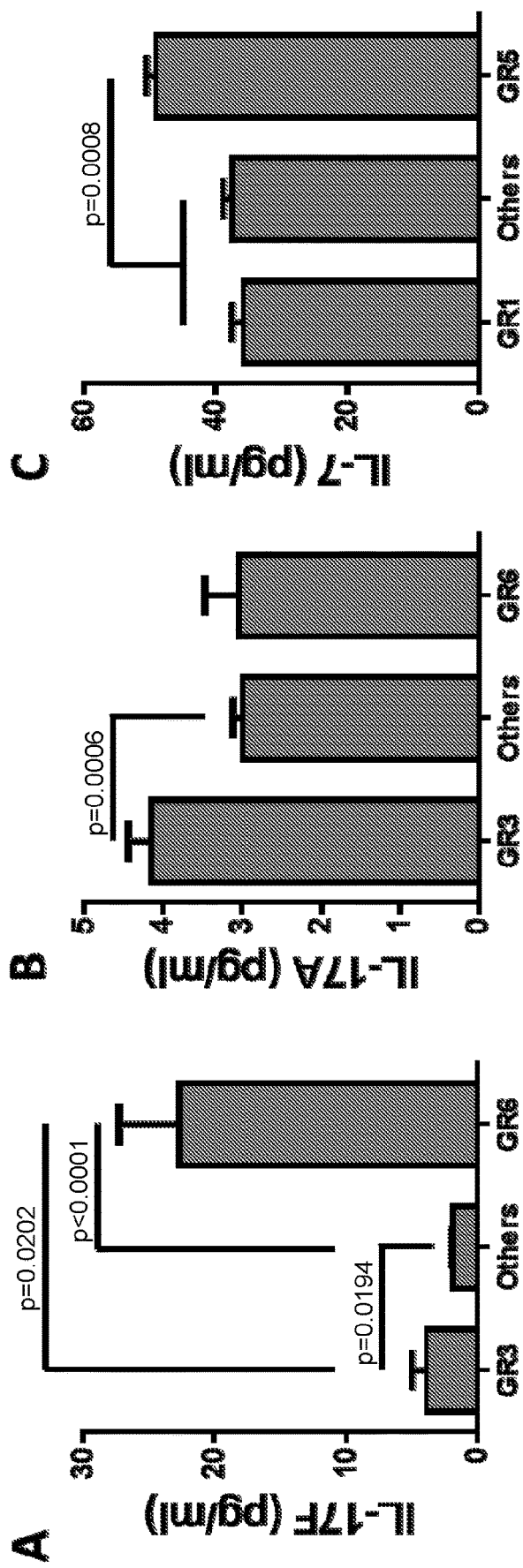
FIG. 4A-4B shows cytokine levels of (A) IL-17F and (B) IL-17A in patients in Group 3, Group 6, and all other groups.
FIG. 4C shows cytokine levels of IL-7 in patients in Group 1, Group 5, and all other groups.

In this current study, Group 3 and Group 6 were two populations of non-responders (FIG. 3). Group 6 had significantly higher levels of IL-17F, whereas Group 3 had significantly higher levels of IL-17A compared to the other patient groups (FIG. 2 and FIGS. 4A and B). Both IL-17A and IL-17F are signature TH17 cytokines, indicating that Group 3 and Group 6 have extreme clinical phenotypes of non-responsiveness with a strong TH17 response. Groups 1 and 5 represent the other end of the clinical extreme because almost all patients in these two groups responded well to IFN-β therapy. Therefore, IL-7 levels between patients in Groups 1 and 5 to the rest of the MS patients were compared. IL-7 was significantly higher in Group 5 compared to both Group 1 and all other patients (FIG. 4C). In the previous study, patients were selected with two extreme clinical responses-based on relapse frequency and steroid use- to IFN-β. Therefore, it is likely that many of the patients selected for that study would have clustered in Group 5 and Group 6. The new data from this larger cohort reinforces the hypothesis that strong TH17 response is a characteristic of non-responders and that high IL-7 levels is a characteristic of subset of responders.

Differential Biological Effects of IFN-β Treatment in the 6 Clustered Groups

Figure 5:
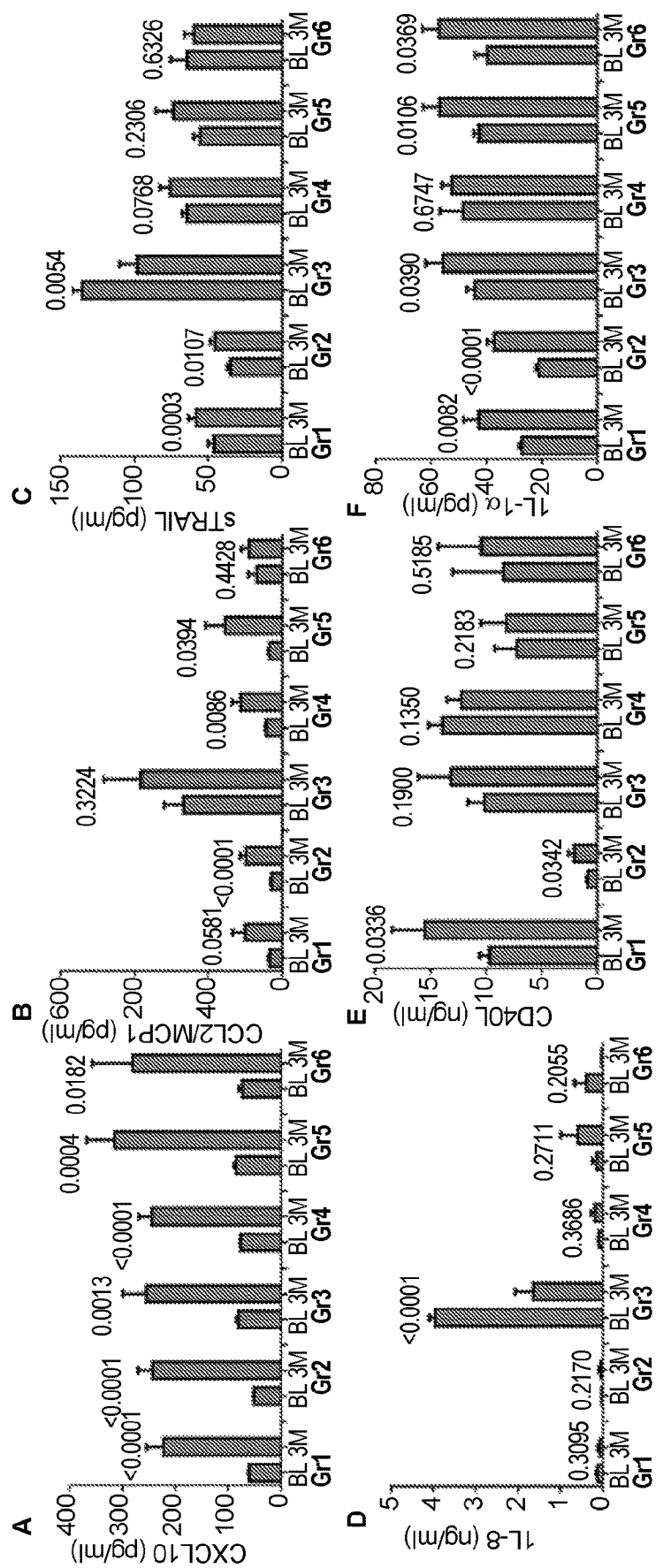
FIG. 5A-5F shows changes in cytokine levels of (A) CXCL10, (B) CCL2/MCP1, (C) sTRAIL, (D) IL-8, (E) CD40L and (F) IL-1α at baseline (BL) and 3 months (3M) following treatment with IFN-β in the 6 distinct subject groups.
Figure 11:
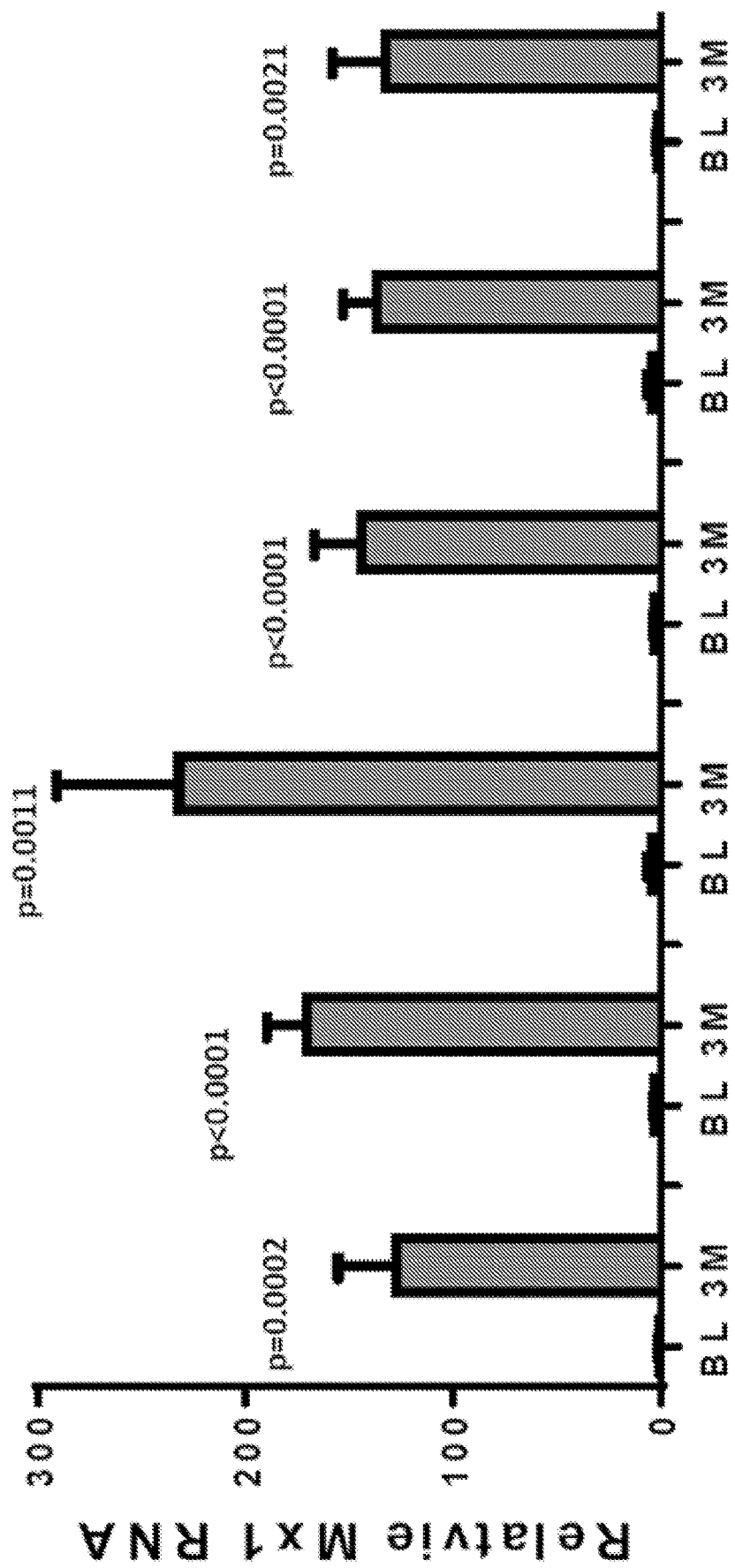
FIG. 11 shows changes in MxA transcription levels from baseline (BL) to 3 months (3M) in the six distinct subject groups.

The biological response to IFN-β therapy in these groups was assessed by observing changes in MxA and cytokine levels between BL and 3M. MxA and CXCL10/IP10, which are transcriptionally controlled by type I IFN were significantly elevated in all 6 RRMS groups at 3M demonstrating that these patients are biologically responding to interferon treatment (FIG. 5A and FIG. 11). However, many differential changes in other cytokines in these groups (Table 11) was observed. Groups 1, 2, 4, and 5 had significant increases in CCL2/MCP1, whereas Groups 3 and 6 had no significant increase in this cytokine (FIG. 5B). sTRAIL, which has been previously associated with good response, was also differentially affected by IFN-β treatment. Groups 1 and 2 had significant increases in TRAIL and there was a trend for increases in Groups 4 and 5 (FIG. 5C). Conversely, sTRAIL was significantly reduced in Group 3 and there was a trending decrease in Group 6 (FIG. 5C). These differences in the induction or inhibition of CCL2 and sTRAIL levels in these groups were striking. Up-regulation of CCL2 and sTRAIL were associated with RRMS groups that responded well to therapy, whereas decreasing sTRAIL and no effects on MCP1 levels were associated with patient groups that did not respond to therapy (FIGS. 3 and 5). Additionally, differential changes in IL-8, CD40L and IL-1α within the groups was observed (FIG. 5D-F). Finally, no patients in Groups 5 and 6 developed neutralizing antibodies to IFN-13 treatment, whereas between 9.4 and 15% of patients in Groups 1 through 5 developed neutralizing antibodies within two years after initiation of therapy (GR1: 17.4%, GR2: 9.4%, GR3: 15.0%, GR4: 10.8%; Table 10).

Traditionally, MS biomarker studies assess differences in molecules in patient groups with clinically defined outcomes. In IFN-β treatment response, there are two major confounders that arise by using this approach for discovery and verification of biomarkers. One confounder is how a study defines response to therapy. Defining response by relapse rates or by EDSS progression results in the discovery of biomarkers that are significantly different in responders and non-responders. The second confounder is that biologically MS is a heterogeneous population; most biomarkers are highly variable in the MS population and do not have a normal Gaussian distribution. In this study, the variability in the serum cytokines was used to stratify the MS patients into subsets. Additionally, these stratified subsets have distinct clinical outcomes to IFN-β therapy.

The first observation was that MS patients with low cytokine concentrations (Group 2) had significantly longer disease duration and greater EDSS before starting IFN-β therapy than the other patients (roughly 7 vs. 4 years). This subset of patients had significant reduction in relapse rates while still having an increase of EDSS score while on IFN-β therapy. This observation suggests that these patients which are obviously in a later disease stage might have fewer inflammatory events and are closer to the progressive phase of the disease.

The second observation was that there are two distinct baseline cytokine profiles that correlate with non-responsiveness defined by having no significant reduction in relapses while on IFN-β therapy. One subset of non-responders (Group 3) had very high levels of IL1β, IL-8, CXCL1/Gro-α, CCL2/MCP1 and IL-17A. This confirms a recent report that baseline levels of IL-1β is significantly elevated in population of patients who do not respond to IFN-β therapy. IL-1β is required for the differentiation of human TH17 cells and furthermore IL-8, CXCL1/Gro-α and CCL2/MCP1 are chemokines induced by IL-17 signaling indicating that the TH17 pathway is elevated in these patients.

The second subset of non-responders (Group 6) had elevated levels of IL-17F, which is similar to a subset of non-responders described in a smaller cohort of patients. Other authors reported that IL-17F levels were not statistically different in responders and non-responders, however, these studies did not consider the heterogeneity in the MS population for their analysis. These studies predefined treatment response by combining the two clinical measures relapse rate and EDSS score (in different ways) and simply compared cytokine concentrations. This might be one of the reasons why the influence IL-17F on treatment response could not be seen.

There is a striking similarity between these two subsets of non-responders; both have characteristics of a TH17 response. One subset of non-responders has high levels of IL-17A and chemokines induced during a TH17 response. The other subset of non-responders has high levels of IL-17F, a signature cytokine of TH17 cells. It is unclear if these two subsets of non-responders represent different pathways of TH17 or are in different stages of a TH17 response. It has been previously shown that TH17 cytokines and granulocyte chemokines are elevated in patients with neuromyelitis optica (NMO), a neuro-inflammatory patient population that does not respond to IFN-β therapy. Disease process in these subsets of IFN-β non-responding MS patients may be similar to NMO.

The third observation was that there are two distinct cytokine profiles that distinguish IFN-β responders; patients with a significant reduction in relapse rates and an arrest in progression of EDSS. One subset of responders, Group 1, had low concentrations of all cytokines except CD40L. This subset of RRMS has a milder inflammatory response, and it may be speculated that this subset can be effectively managed with IFN-β treatment. The other subset of responders (Group 5) had high levels of IL-7 compared to the other MS subsets. A previous report described a different smaller cohort in which there was an association of high IL-7 levels with efficacious IFN-β therapy. Genome wide association studies provided evidence that IL-7 signaling may have protective effects in RRMS. Two studies identified a polymorphism the IL-7R gene that confers risk for RRMS. This polymorphism encodes for a splice variant of IL-7R that generates a soluble version of this receptor. The soluble IL-7R would act as a molecular decoy, decrease signals initiated by IL-7 and contribute to the development of RRMS. The protective role IL-7 plays during IFN-β treatment is not entirely clear. However, previous reports have described that IL-7 promotes TH1 differentiation and IFN-γ expression, which are both critical for the protective effects of IFN-β in experimental autoimmune encephalomyelitis.

Finally, each RRMS group up-regulated MxA and CXCL10/IP10 after 3 months of therapy, demonstrating that patients are biologically responding to therapy. However, other cytokines had differential changes with IFN-β treatment. Notably, sTRAIL and CCL2/MCP1 are significantly increased by IFN-β treatment in the patient subsets that responded well to therapy but not in subsets that were non-responders. This demonstrates that all subsets of patients responded biologically to IFN-β but that the differential characteristics of subsets of patients influence the efficacy of the therapy.

The heterogeneous nature of RRMS has been most notably described by Lucchinetti et al and Han et al through the analysis of lesions from autopsy and biopsy tissues from MS patients. These reports described subgroups of RRMS patients that had fundamental differences in immunopathological patterns within lesions. The data from serum cytokines, as presented herein, provides more evidence that there are immunologically distinct subgroups of MS. Additionally, these subgroups can be used to stratify treatment response and prognosis of MS patients. Such stratification of RRMS populations provides evidence that serum biomarkers can be discovered that are informative for predicting prognosis and treatment response in this disease.

Materials and Methods

Patients and Specimens

The prospective European multicenter study NABINMS (Neutralizing antibodies on Interferon beta in Multiple Sclerosis) was conducted by 22 clinical centers in Austria, Denmark, Italy, the Netherlands, Spain and Switzerland and enrolled patients with clinically isolated syndrome (CIS) or RRMS fulfilling the revised McDonalds criteria 2005 between June 2006 and August 2009. Inclusion criteria were age greater than 18 years and a medical indication for first-time IFNβ treatment. Exclusion criteria were prior IFN-β treatment or any contraindication to the therapy.

Eligible patients received one of the three available IFN-β preparations: intramuscular IFN-β-1a (Avonex®, Biogen Idec, Cambridge, Mass., USA), subcutaneous (SC) IFNβ-1a (Rebif® 22 or 44 µg, Merck Serono, Geneva, Switzerland) or SC IFN-β-1b (Betaferon®, Bayer Schering, Berlin, Germany). Cytokine levels were assessed from patients who had available data on relapse rates two years prior to and two years post initiation of IFN-β therapy, resulting in a total number of 157 patients. Blood samples (analyzed for cytokines) were collected by peripheral venous puncture at baseline, immediately before the first IFN-β injection, and at follow-up after 3 months±2 weeks (3M) within 4 to 12 hours post-injection. Clinical assessments (number of relapses and determination of the EDSS score) were performed at baseline, 3M, 12 months±4 weeks and 24 months±4 weeks after initiation of therapy. A relapse was defined as patient-reported symptoms or objectively observed signs typical of an acute inflammatory demyelinating event in the central nervous system, current or prior to the visit, with duration of at least 24 hours, in the absence of fever or infection. Serum was isolated from blood by centrifugation, after the blood samples were allowed to clot for ≥30 minutes. Frozen serum samples were shipped on dry ice to Stanford University where they were stored at −80° C. until analysis.

Serum Cytokines Measurements

Cytokine measurements were performed in the Human Immune Monitoring Center at Stanford University. Human 51-multiplex Luminex assays were purchased from eBiosciences/Affymetrix and used according to the manufacturer's recommendations with modifications as described below. Briefly, beads were added to a 96 well plate and washed in a Biotek ELx405 washer. Samples were added to the plate containing the mixed antibody-linked beads and incubated at room temperature for 1 hour followed by overnight incubation at 4° C. with shaking. Cold and room temperature incubation steps were performed on an orbital shaker at 500-600 rpm. Following the overnight incubation plates were washed in a Biotek ELx405 washer and then biotinylated analyte-specific detection antibody was added for 75 minutes at room temperature with shaking. Plate was washed as above and streptavidin-phycoerythrin was added. After incubation for 30 minutes at room temperature wash was performed as above and reading buffer was added to the wells. Each sample was measured in duplicate. Plates were read using a Luminex 200 instrument with a lower bound of 50 beads per sample per cytokine. Custom assay Control beads by Radix Biosolutions are added to all wells. Table 12 illustrates the serum biomarkers as well as their respective accession numbers.

Nab Assay:

NAbs were measured by a luciferase assay using human fibrosarcoma cells. These cells express IFNβ receptors on their surface and have been stably transfected with a luciferase reporter gene cassette. Upon binding of IFNβ, luciferase is produced in a predictable dose-dependent manner and diminished in the presence of NAbs. Detailed assay description can be found elsewhere.

Mxa Assay:

MxA was determined at the mRNA level. Briefly, RNA was isolated from whole blood samples, converted to cDNA and subjected to real-time polymerase chain reaction (rtPCR) for MxA quantification.

Statistical and Cluster Analysis:

For comparison of cytokine differences between responders and non-responders, cytokine values were $\log_2$-transformed, and P-values along with odds ratios (OR) and 95% confidence interval (CI) were calculated for each cytokine using logistic regression in R version 3.1.2 (http://www.r-project.org/). Absolute values were shown as mean±standard error of the mean (SEM) (in the figures) or ±standard deviation (in the tables). For cluster analysis of baseline cytokines, the cytokines with the most variability in the RRMS samples were selected. To this end, the coefficient of variation (CV) of each cytokine in all serum samples, including baseline and 3M, was determined by dividing the standard deviation by the mean and multiplying by 100 to give a percent variability. Interleukin (IL)-1β, IFN-α, IL-1RA, CXCL1/Gro-α, IL-8, CCL3/MIP1α, IFN-β, IL-17F, G-CSF, CCL2/MCP1, LIF, CD40L, IL-6, CXCL10/IP10 had CV values above 100% and were used to perform hierarchical clustering of baseline serum samples. Using Gene Cluster software, the cytokine values were normalized and centered to the mean, and each sample was then ordered by complete linkage clustering. The results were presented as a heat map using TreeView. Differences in individual baseline cytokine concentrations in the resulting groups were assessed using a Kruskal-Wallis test with a Dunn's multiple comparisons test in Prism version 6 (GraphPad Software, Inc., La Jolla, Calif.). Differences of cytokine concentration between baseline and month 3 were analyzed using paired t-tests in Prism. Comparisons of baseline demographic and clinical features within the clustered groups were performed using Mann Whitney tests and non-parametric ANOVAs with Dunn's multiple comparisons or Chi-square tests in Prism. To assess treatment effects in each group, the changes in EDSS and number of relapses before initiation of therapy to two years after initiation of therapy were assessed in each group using paired t-tests in Prism.

Standard Protocol Approvals and Patient Consents:

The study protocol was approved by the local ethic committees (approval number AM2538 239/4.8) of all participating centers. Prior to any study-related investigations, written informed consent was obtained from all patients. All patient related data (as well as samples that were shipped for cytokine measurement to Stanford University) were used in an anonymized fashion.

TABLE 1

Relapse response in patient groups defined by baseline cytokines.

|  | Group 1 | Group 5 | Not 1 and 5 | P-value |
| --- | --- | --- | --- | --- |
| Non Resp/Resp | 5/18 | 1/15 | 61/57 | 0.0002 |
| (% Non Resp) | 21.74% | 6.25% | 51.69% |  |
|  | Group 3 | Group 6 | Not 3 and 6 | P-value |
| Non Resp/Resp | 13/7 | 5/3 | 49/80 | 0.0384 |
| (% Non Resp) | 65.00% | 62.50% | 37.98% |  |

Note:
Non Resp = Non responder, Resp = Responder.
A responder was defined as having no relapses after the initiation of IFN-β therapy.
P-values were evaluated using Chi-square tests

TABLE 2

Baseline clinical and demographic data of relapse responders (Resp) and non-responders (Non Resp).

| Variable | Resp | Non Resp | P-values |
| --- | --- | --- | --- |
| n | 90 | 67 |  |
| Diagnosis [RR/CIS (% RR)] | 64/26 (71.1) | 50/17 (74.6) | 0.6251[a] |
| Age (SD) | 37.1 (8.7) | 35.6 (8.7) | 0.2622[b] |
| Disease Duration (SD) | 4.9 (6.1) | 4.7 (5.8) | 0.5585[b] |

TABLE 2-continued

Baseline clinical and demographic data of relapse responders (Resp) and non-responders (Non Resp).

| Variable | Resp | Non Resp | P-values |
|---|---|---|---|
| Sex F/M (% F) | 59/31 (65.5) | 49/18 (73.1) | 0.3107[a] |
| Baseline EDSS (SD) | 1.6 (1.3) | 1.7 (1.4) | 0.4165[b] |
| # of Relapses (SD) | 1.3 (0.7) | 1.6 (0.7) | 0.0074[b] |
| IFN Prep [n (%)] | | | |
| IM IFNb-1a | 46 (51.1) | 32 (47.8) | |
| SC IFNb-1b | 18 (20.0) | 18 (26.9) | 0.5917[a] |
| SC IFNb-1a | 26 (28.9) | 17 (25.4) | |

Notes:

RR = Relapsing Remitting, CIS = Clinically isolated syndrome, SD = Standard deviation.

Responders were defined as having no relapses during the 2 years post initiation of IFN-β Therapy.

P-values were evaluated using [a]Chi square tests or [b]Mann Whitney T-tests.

TABLE 3

Differences in baseline cytokine concentrations in relapse responders and non-responders.

| | Risk of Relapse while on IFN-β therapy | |
|---|---|---|
| Cytokine | OR (95% CI) | P |
| IL1β | 1.45 (1.09-1.93) | 0.0105 |
| CCL2/MCP1 | 1.3 (0.98-1.72) | 0.0672 |
| LIF | 0.85 (0.7-1.04) | 0.1138 |
| IL1RA | 1.14 (0.95-1.36) | 0.1603 |
| IL-8 | 1.07 (0.97-1.18) | 0.1773 |
| TNFβ | 0.68 (0.38-1.22) | 0.1982 |
| CXCL1/Groα | 1.2 (0.9-1.6) | 0.2143 |
| MIP1α | 1.16 (0.91-1.48) | 0.2394 |
| IL-13 | 0.74 (0.44-1.23) | 0.2465 |
| IL-5 | 0.77 (0.49-1.21) | 0.2592 |
| Eotaxin | 0.8 (0.52-1.22) | 0.2958 |
| TNFα | 0.68 (0.33-1.42) | 0.3065 |
| PAI | 1.4 (0.73-2.71) | 0.3149 |
| NGF | 0.85 (0.61-1.17) | 0.3176 |
| IL-17F | 1.19 (0.83-1.71) | 0.3421 |
| IL-10 | 0.82 (0.55-1.24) | 0.3447 |
| Resistin | 1.15 (0.86-1.53) | 0.3565 |
| IP10 | 0.67 (0.28-1.58) | 0.3574 |
| IL12p40 | 0.85 (0.59-1.22) | 0.3762 |
| IL12p70 | 0.83 (0.56-1.25) | 0.3815 |
| IL-7 | 0.78 (0.44-1.39) | 0.4064 |
| IL-1α | 0.82 (0.5-1.32) | 0.4122 |
| GMCSF | 0.85 (0.55-1.29) | 0.4406 |
| MIP1β | 1.3 (0.66-2.56) | 0.4429 |
| IFNβ | 1.13 (0.83-1.54) | 0.4465 |
| IL-2 | 0.83 (0.5-1.37) | 0.4576 |
| IL-4 | 0.82 (0.46-1.46) | 0.4898 |
| HGF | 0.87 (0.59-1.28) | 0.4901 |
| PDGF | 0.86 (0.57-1.32) | 0.4923 |
| VCAM | 1.09 (0.84-1.42) | 0.5078 |
| Rantes | 1.08 (0.87-1.34) | 0.5122 |
| ICAM | 1.07 (0.86-1.35) | 0.5309 |
| CD40L | 0.97 (0.87-1.08) | 0.5373 |
| VEGF | 0.9 (0.64-1.26) | 0.5399 |
| IL-6 | 1.18 (0.69-2.01) | 0.5428 |
| IFNα | 0.94 (0.76-1.16) | 0.5469 |
| Leptin | 0.88 (0.55-1.42) | 0.6129 |
| GCSF | 1.05 (0.86-1.28) | 0.6247 |
| TGFβ | 0.89 (0.54-1.45) | 0.6325 |
| IL-15 | 0.92 (0.65-1.32) | 0.6640 |
| sFasL | 0.88 (0.48-1.6) | 0.6662 |
| ENA | 1.1 (0.7-1.74) | 0.6696 |
| TGFα | 0.91 (0.58-1.42) | 0.6754 |
| SCF | 0.8 (0.28-2.28) | 0.6808 |
| MCSF | 1.11 (0.68-1.79) | 0.6808 |
| MCP3 | 0.92 (0.62-1.38) | 0.6961 |
| FGF | 0.88 (0.44-1.75) | 0.7129 |
| IFNγ | 0.89 (0.46-1.71) | 0.7305 |
| IL-17 | 0.96 (0.69-1.32) | 0.7877 |
| MIG | 1.01 (0.84-1.22) | 0.9162 |
| sTRAIL | 0.99 (0.74-1.32) | 0.9280 |

Note:

Baseline cytokine values were 2-log transformed. Odds ratios and p-values were assessed using logistic regression.

TABLE 4

Serum cytokine concentration with statistically significant changes from Baseline to 3 months in relapse responders and non-responders.

| Cytokine (pg/ml) | Baseline | | 3 Month | | Δ from BL to 3 M | |
|---|---|---|---|---|---|---|
| | Mean | SD | Mean | SD | pvalue | Direction |
| Responders (n = 90) | | | | | | |
| IP10 | 68.0 | 17.1 | 246.5 | 181.4 | <0.0001 | up |
| CCL2/MCP1 | 49.4 | 72.0 | 125.2 | 202.4 | 0.0006 | up |
| IL-1α | 36.2 | 34.8 | 46.5 | 22.7 | 0.0135 | up |
| IFNβ | 6.3 | 13.7 | 11.4 | 26.4 | 0.0179 | up |
| GCSF | 3.5 | 4.6 | 5.1 | 6.7 | 0.0191 | up |
| TGFβ | 21.7 | 10.0 | 24.3 | 12.4 | 0.0216 | up |
| ICAM | 23924.4 | 18247.1 | 25790.5 | 18162.8 | 0.0242 | up |
| IL12p40 | 73.2 | 29.9 | 79.4 | 34.8 | 0.0246 | up |
| MIP1β | 1254.8 | 409.8 | 1361.0 | 622.6 | 0.0287 | up |
| sTRAIL | 56.3 | 29.0 | 64.0 | 33.4 | 0.0290 | up |
| CD40L | 7594.1 | 7727.2 | 9420.8 | 10852.4 | 0.0315 | up |
| IL1RA | 617.4 | 1211.9 | 1665.2 | 4627.5 | 0.0382 | up |
| MIP1α | 59.6 | 70.8 | 88.6 | 143.2 | 0.0453 | up |
| VCAM | 11249.3 | 5327.1 | 12828.1 | 9064.8 | 0.0498 | up |
| Non Responders (N = 67) | | | | | | |
| IP10 | 65.8 | 18.2 | 256.8 | 197.8 | <0.0001 | up |
| IL-1α | 32.4 | 14.3 | 47.5 | 25.6 | <0.0001 | up |
| IFNβ | 7.0 | 10.5 | 10.5 | 16.4 | 0.0004 | up |
| IFNα | 59.5 | 57.5 | 86.4 | 71.5 | 0.0024 | up |
| CCL2/MCP1 | 91.2 | 150.2 | 167.9 | 251.8 | 0.0124 | up |
| VCAM | 11866.4 | 6006.0 | 13284.5 | 6496.9 | 0.0149 | up |
| IL-8 | 859.3 | 1589.7 | 488.7 | 1211.5 | 0.0198 | down |
| TNFβ | 18.2 | 6.1 | 19.8 | 7.8 | 0.0413 | up |

Note:

P-values were determined using a paired t-test.

*Up = increase in concentration; Down = decrease in concentration.

TABLE 5

Baseline clinical and demographic data of EDSS responders (Resp) and non-responders (Non Resp).

| Variable | Resp | Non Resp | P-values |
|---|---|---|---|
| n | 114 | 39 | |
| Diagnosis [RR/CIS (% RR)] | 80/34 (70.2) | 31/8 (79.5) | 0.2607[a] |
| Age (SD) | 36.1 (9.0) | 36.9 (7.6) | 0.5697[b] |
| Disease Duration (SD) | 4.6 (6.2) | 5.5 (5.3) | 0.0817[b] |
| Sex F/M (% F) | 81/33 (71.1) | 26/13 (66.7) | 0.6061[a] |
| Baseline EDSS (SD) | 1.8 (1.2) | 1.2 (1.6) | 0.0034[b] |
| # of Relapses (SD) | 1.5 (0.7) | 1.4 (0.7) | 0.7348[b] |

TABLE 5-continued

Baseline clinical and demographic data of EDSS responders (Resp) and non-responders (Non Resp).

| Variable | Resp | Non Resp | P-values |
|---|---|---|---|
| IFN Prep [n (%)] | | | |
| IM IFNb-1a | 58 (51.0) | 19 (47.8) | |
| SC IFNb-1b | 25 (22.0) | 9 (23.1) | 0.9729[a] |
| SC IFNb-1a | 31 (27.2) | 11 (28.2) | |

Notes:
RR = Relapsing Remitting, CIS = Clinically isolated syndrome, SD = Standard deviation.
Responders were defined as having no relapses during the 2 years post initiation of IFN-β Therapy.
P-values were evaluated using [a]Chi square tests or [b]Mann Whitney T-tests.

TABLE 6

Differences in baseline cytokine concentrations in EDSS responders and non-responders.

| | Risk of increasing EDSS while on IFNβ | |
|---|---|---|
| Cytokine | OR (95% CI) | P |
| MIG | 0.81 (0.66-1) | 0.0485 |
| TNFβ | 0.61 (0.32-1.16) | 0.1308 |
| PAI | 0.56 (0.25-1.23) | 0.1471 |
| CXCL1/Groα | 0.75 (0.51-1.11) | 0.1489 |
| IL1RA | 0.84 (0.66-1.07) | 0.1667 |
| VEGF | 0.77 (0.52-1.12) | 0.1696 |
| IL-8 | 0.92 (0.81-1.04) | 0.1990 |
| PDGF | 0.75 (0.47-1.2) | 0.2293 |
| IL-1β | 0.83 (0.6-1.14) | 0.2490 |
| MCP3 | 0.77 (0.49-1.2) | 0.2495 |
| MIP1α | 0.85 (0.64-1.14) | 0.2847 |
| ENA | 0.76 (0.45-1.27) | 0.2919 |
| MIP1β | 0.66 (0.8-1.46) | 0.3097 |
| HGF | 0.79 (0.5-1.25) | 0.3199 |
| CXCL1/MCP1 | 0.85 (0.61-1.19) | 0.3388 |
| Eotaxin | 0.79 (0.49-1.29) | 0.3451 |
| IL-6 | 0.74 (0.38-1.42) | 0.3652 |
| Rantes | 0.91 (0.74-1.12) | 0.3674 |
| IL-7 | 0.74 (0.39-1.42) | 0.3690 |
| IL12p40 | 0.84 (0.56-1.24) | 0.3804 |
| LIF | 0.91 (0.73-1.13) | 0.3856 |
| sFasL | 0.77 (0.39-1.51) | 0.4397 |
| IL-2 | 0.8 (0.45-1.42) | 0.4526 |
| IL-4 | 0.8 (0.42-1.54) | 0.5066 |
| IL-1α | 0.83 (0.48-1.44) | 0.5129 |
| IL-5 | 0.85 (0.51-1.42) | 0.5393 |
| CD40L | 0.96 (0.65-1.09) | 0.5561 |
| IP10 | 0.76 (0.28-2.02) | 0.5786 |
| MCSF | 0.87 (0.53-1.44) | 0.5985 |
| TNFα | 0.81 (0.86-1.83) | 0.6085 |
| ICAM | 1.06 (0.81-1.39) | 0.6504 |
| Leptin | 0.89 (0.52-1.54) | 0.6825 |
| SCF | 0.79 (0.24-2.56) | 0.6922 |
| NGF | 0.95 (0.66-1.35) | 0.7590 |
| GCSF | 0.97 (0.76-1.22) | 0.7707 |
| IFNγ | 0.91 (0.42-1.94) | 0.8004 |
| GMCSF | 0.94 (0.58-1.52) | 0.8046 |
| IFNα | 0.97 (0.76-1.24) | 0.8058 |
| IL-17 | 0.96 (0.67-1.38) | 0.8354 |
| IL12p70 | 0.96 (0.61-1.51) | 0.8535 |
| IL-10 | 0.96 (0.61-1.53) | 0.8775 |
| FGF | 0.95 (0.43-2.08) | 0.8945 |
| IL-17F | 0.97 (0.64-1.47) | 0.8965 |
| sTRAIL | 1.02 (0.73-1.43) | 0.9009 |
| Resistin | 0.99 (0.74-1.31) | 0.9191 |
| VCAM | 1.01 (0.77-1.33) | 0.9269 |
| TGFα | 0.98 (0.59-1.64) | 0.9486 |
| IL-13 | 0.99 (0.55-1.78) | 0.9744 |
| IL-15 | 0.99 (0.66-1.49) | 0.9750 |
| TGFβ | 1 (0.57-1.76) | 0.9917 |
| IFNβ | 1 (0.7-1.43) | 0.9928 |

Note:
EDSS non-responders were defined as having an increase of 1 EDSS point from baseline to 2 years post initiation of therapy. Baseline cytokine values were 2-log transformed odds ratios and p-values were assessed using logistic regression.

TABLE 7

Serum cytokine concentration with statistically significant changes from Baseline to 3 months in EDSS responders and non-responders.

| Cytokine | Baseline Mean | Baseline SD | 3 Month Mean | 3 Month SD | Δ from BL to 3 M pvalue | Direction |
|---|---|---|---|---|---|---|
| Responders (n = 114) | | | | | | |
| IP10 | 67.38 | 17.64 | 244.32 | 177.31 | <0.0001 | up |
| MCP1 | 74.54 | 130.55 | 154.52 | 249.97 | 0.0007 | up |
| IL-1a | 35.42 | 31.77 | 46.80 | 23.28 | 0.0010 | up |
| IFNB | 6.47 | 12.84 | 11.68 | 25.89 | 0.0029 | up |
| PAI | 3003.00 | 1400.61 | 2722.56 | 621.82 | 0.0121 | down |
| CD40L | 7666.54 | 8047.95 | 9529.21 | 11399.68 | 0.0161 | up |
| IL-8 | 646.04 | 1392.37 | 383.25 | 1068.58 | 0.0190 | down |
| IL17 | 3.10 | 1.49 | 3.37 | 1.77 | 0.0277 | up |
| ENA | 1342.11 | 576.62 | 1233.78 | 569.99 | 0.0406 | down |
| NGF | 35.20 | 14.75 | 37.83 | 17.62 | 0.0426 | up |
| HGF | 85.95 | 68.25 | 74.27 | 40.10 | 0.0435 | down |
| Non Responders (N = 39) | | | | | | |
| IP10 | 65.88 | 18.10 | 269.81 | 224.20 | <0.0001 | up |
| IL-1a | 32.26 | 13.83 | 47.60 | 26.99 | 0.0001 | up |
| VCAM | 10718.00 | 4749.01 | 12535.83 | 5338.01 | 0.0015 | up |
| MCP1 | 45.45 | 35.28 | 112.96 | 140.75 | 0.0041 | up |
| IFNB | 7.28 | 11.82 | 9.43 | 9.76 | 0.0136 | up |

Note:
P-values were determined using a paired t-test.
*Up = increase in concentration; Down = decrease in concentration.

TABLE 8

Variability in serum cytokines in all RRMS samples.

| Cytokine | Mean | Stdev | CV |
|---|---|---|---|
| IL-1β | 15.18178 | 85.38205 | 562.398 |
| IFNα | 92.82164 | 282.0426 | 303.8543 |
| IL1RA | 1592.452 | 4373.452 | 274.6364 |
| CXCL1/Groα | 28.53919 | 73.52668 | 257.6341 |
| IL-8 | 466.6038 | 1201.103 | 257.414 |
| MIP1α | 87.7992 | 183.8879 | 209.4415 |
| IFNβ | 8.79136 | 18.32557 | 208.4497 |
| IL-17F | 3.439355 | 7.149955 | 207.8865 |
| GCSF | 4.995596 | 9.486231 | 189.8919 |
| CCL2/MCP1 | 105.3178 | 182.0219 | 172.8311 |
| LIF | 9.168905 | 12.11207 | 132.0995 |
| CD40L | 8152.059 | 9357.037 | 114.7813 |
| IL-6 | 161.4753 | 182.7868 | 113.198 |
| IP10 | 158.9792 | 162.0083 | 101.9054 |
| TGFα | 28.04252 | 23.93896 | 85.36666 |
| Rantes | 1196.324 | 913.6358 | 76.37026 |
| MIG | 66.54243 | 50.791 | 76.32874 |
| ICAM | 24096.02 | 18070.9 | 74.99537 |
| VEGF | 74.90045 | 52.87619 | 70.59529 |
| HGF | 77.903 | 53.22889 | 68.32714 |

TABLE 8-continued

Variability in serum cytokines in all RRMS samples.

| Cytokine | Mean | Stdev | CV |
|---|---|---|---|
| IL-1α | 40.76071 | 26.71024 | 65.52938 |
| IFNγ | 4.28972 | 2.719826 | 63.40339 |
| TNFβ | 19.93169 | 12.5423 | 62.92644 |
| sTRAIL | 62.2846 | 38.80343 | 62.3002 |
| Resistin | 2605.451 | 1590.732 | 61.054 |
| VCAM | 12264.53 | 6971.499 | 56.84279 |
| IL12p70 | 121.1801 | 67.3262 | 55.5588 |
| IL-17 | 32.58402 | 18.0982 | 55.54318 |
| GMCSF | 54.67159 | 29.89452 | 54.68017 |
| MCP3 | 41.24495 | 22.38827 | 54.28123 |
| IL-2 | 50.35949 | 26.59118 | 52.80272 |
| IL-10 | 24.61486 | 12.78802 | 51.95244 |
| IL-15 | 26.51929 | 13.51781 | 50.97352 |
| IL-7 | 38.44577 | 19.30628 | 50.21693 |
| Leptin | 2344.315 | 1169.727 | 49.89632 |
| IL-5 | 171.7358 | 84.972 | 49.47832 |
| TGFβ | 22.64879 | 10.8607 | 47.95269 |
| Eotaxin | 38.60524 | 18.50225 | 47.92678 |
| IL12p40 | 74.96423 | 35.52513 | 47.38945 |
| NGF | 36.62356 | 17.24343 | 47.08289 |
| PDGF | 2479.453 | 1158.717 | 46.73277 |
| ENA | 1273.79 | 573.886 | 45.05344 |
| IL-4 | 17.65607 | 7.584387 | 42.95625 |
| IL-13 | 28.74356 | 12.29113 | 42.76136 |
| MIP1β | 1325.875 | 546.8478 | 41.2443 |
| PAI | 2813.971 | 1068.451 | 37.9695 |
| MCSF | 53.84071 | 18.41836 | 34.20899 |
| FGF | 69.67874 | 23.74226 | 34.07389 |
| sFasL | 49.45654 | 16.76712 | 33.90274 |
| TNFα | 222.9109 | 74.15677 | 33.26745 |
| SCF | 552.0407 | 116.3982 | 21.08507 |

Note:
Stdev = Standard deviation, CV = Co-efficient of variation.

TABLE 9

Baseline clinical and demographic data of patients grouped by cytokine clusters.

| Baseline Characteristics | Group 1 | Group 2 | Group 3 | Group 4 | Group 5 | Group 6 | P-values |
|---|---|---|---|---|---|---|---|
| n | 23 | 53 | 20 | 37 | 16 | 8 | |
| Diagnosis [RR/CIS (% RR)] | 15/8 (65.2) | 43/10 (81.1) | 13/7 (65.0) | 26/11 (70.2) | 12/4 (75.0) | 5/3 (62.5) | 0.5920[a] |
| Age (SD) | 37.4 (6.8) | 38.0 (8.7) | 33.5 (9.3) | 35.0 (9.0) | 36.1 (10.1) | 38.1 (7.6) | 0.4256[b] |
| Disease Duration (SD) | 4.3 (5.0) | 6.6 (7.8) | 3.5 (4.3) | 4.1 (5.1) | 3.4 (3.3) | 3.0 (3.7) | 0.3060[c] |
| Sex F/M (% F) | 15/8 (65.2) | 37/15 (71.2) | 13/7 (65.0) | 29/8 (78.4) | 9/7 (56.3) | 5/3 (62.5) | 0.6506[c] |
| Baseline EDSS (SD) | 1.3 (1.4) | 1.9 (1.5) | 1.8 (1.4) | 1.3 (1.0) | 1.5 (1.1) | 1.2 (1.4) | 0.1790[c] |
| # of Relapses (SD) | 1.3 (0.7) | 1.5 (0.7) | 1.6 (0.7) | 1.3 (0.7) | 1.4 (0.7) | 1.9 (0.8) | 0.2647[b] |
| IFN Prep [n (%)] | | | | | | | |
| IM IFNb-1a | 11 (47.8) | 30 (50.8) | 10 (50.0) | 15 (40.5) | 8 (50.0) | 4 (50.0) | |
| SC IFNb-1b | 5 (21.7) | 12 (20.3) | 6 (30.0) | 16 (43.2) | 1 (6.3) | 2 (25.0) | 0.2754[c] |
| SC IFNb-1a | 7 (30.4) | 17 (28.8) | 4 (20.0) | 6 (16.2) | 7 (43.8) | 2 (25.0) | |

Notes:
SD = Standard deviation.
P-values were evaluated using [a] Chi square tests or [b] Kruskal Wallis tests with Dunn's multiple comparisons.

TABLE 10

Patients that switch off IFN-β or develop neutralizing antibodies to IFN-β by 24 months post initiation of therapy.

| | Group 1 | Group 2 | Group 3 | Group 4 | Group 5 | Group 6 | P-values |
|---|---|---|---|---|---|---|---|
| n | 23 | 53 | 20 | 37 | 16 | 8 | |
| Switching off IFN [IFN off/on (% off)] | 6/17 (26.1) | 9/44 (17.0) | 4/16 (20.0) | 10/27 (27.0) | 2/14 (12.5) | 1/7 (12.5) | 0.7359 |
| NAbs [pos/neg (% pos)] | 4/19 (17.4) | 5/48 (9.4) | 3/17 (15.0) | 4/33 (10.8) | 0/16 (0) | 0/8 (0) | 0.4692 |

Notes:
NAbs = neutralizing antibodies to IFN-β.
P-values were evaluated using Chi square tests.

TABLE 11

Serum cytokine concentrations with statistically significant changes from Baseline to 3 months in the six groups of MS patients.

| TNFβ | | Group 1 (N = 23) | | | | | |
|---|---|---|---|---|---|---|---|
| MCP3 | Cytokine | Baseline | | 3 Month | | Δ from BL to 3 M | |
| ICAM | (pg/ml) | Mean | SD | Mean | SD | pvalue | Direction* |
| CD40L | IP10 | 61.09 | 6.73 | 222.07 | 154.71 | <0.0001 | up |
| TGFα | IFNβ | 3.11 | 1.66 | 6.35 | 3.40 | <0.0001 | up |
| SCF | sTRAIL | 45.93 | 20.29 | 57.93 | 26.06 | 0.0003 | up |
| Cytokine | IL1RA | 371.10 | 335.23 | 1048.03 | 1273.95 | 0.0039 | up |
| (pg/ml) | IL-1α | 27.27 | 4.97 | 42.69 | 27.37 | 0.0082 | up |

TABLE 11-continued

Serum cytokine concentrations with statistically significant changes from Baseline to 3 months in the six groups of MS patients.

| | Cytokine (pg/ml) | Baseline Mean | Baseline SD | 3 Month Mean | 3 Month SD | pvalue | Direction |
|---|---|---|---|---|---|---|---|
| IL-8 | VCAM | 11478.68 | 4664.78 | 13090.41 | 4468.74 | 0.0103 | up |
| IP10 | IFNα | 30.41 | 28.81 | 54.82 | 58.47 | 0.0198 | up |
| IL-17 | CD40L | 9658.91 | 4370.82 | 15522.04 | 14217.97 | 0.0336 | up |
| VEGF | IL-17F | 1.63 | 0.81 | 1.93 | 1.01 | 0.0422 | up |
| Resistin | MIG | 45.97 | 32.49 | 61.63 | 38.68 | 0.0486 | up |
| MIG | CCL2/MCP1 | 34.97 | 17.09 | 100.42 | 163.13 | 0.0518 | up |

Group 2 (N = 53)

| | Cytokine (pg/ml) | Baseline Mean | Baseline SD | 3 Month Mean | 3 Month SD | pvalue | Direction |
|---|---|---|---|---|---|---|---|
| sTRAIL | | | | | | | |
| sFasL | | | | | | | |
| IL12p40 | | | | | | | |
| Eotaxin | IP10 | 51.95 | 9.51 | 242.71 | 208.15 | <0.0001 | up |
| PAI | CCL2/MCP1 | 30.44 | 17.21 | 98.54 | 108.29 | <0.0001 | up |
| ICAM | IL-1α | 21.30 | 7.61 | 37.15 | 18.63 | <0.0001 | up |
| TNFβ | IFNβ | 3.16 | 2.21 | 5.59 | 2.99 | <0.0001 | up |
| IL-1α | IFNα | 30.83 | 23.08 | 74.39 | 63.03 | <0.0001 | up |
| HGF | IL12p40 | 42.54967 | 21.0874 | 53.64724 | 27.13676 | 0.0002 | up |
| Cytokine | NGF | 21.49 | 10.68 | 26.92 | 13.38 | 0.0004 | up |
| (pg/ml) | MIG | 33.62 | 27.33 | 59.85 | 57.69 | 0.0007 | up |
| IP10 | IL-10 | 14.87 | 6.60 | 17.75 | 8.37 | 0.0010 | up |
| IFNβ | IL-15 | 15.40 | 7.74 | 18.80 | 10.29 | 0.0012 | up |
| PDGF | Eotaxin | 24.61 | 14.80 | 29.99 | 16.32 | 0.0014 | up |
| HGF | VCAM | 8987.17 | 3694.95 | 10477.14 | 3481.67 | 0.0016 | up |
| CCL2/MCP1 | IL-1β | 0.87 | 0.07 | 0.91 | 0.13 | 0.0017 | up |
| VEGF | CXCL1/Groα | 10.29 | 3.99 | 13.42 | 7.61 | 0.0020 | up |
| Eotaxin | VEGF | 38.85 | 19.16 | 47.36 | 25.25 | 0.0026 | up |
| ENA | MIP1α | 29.21 | 19.79 | 41.32 | 30.34 | 0.0027 | up |
| TGFα | IL1RA | 166.13 | 78.16 | 792.29 | 1473.91 | 0.0029 | up |
| IL-7 | IL17 | 2.39 | 1.23 | 2.81 | 1.62 | 0.0036 | up |
| IL-5 | GMCSF | 32.75 | 13.71 | 38.95 | 17.20 | 0.0045 | up |
| IL-4 | LIF | 1.72 | 2.60 | 3.41 | 4.63 | 0.0047 | up |
| Cytokine | MIP1β | 997.83 | 249.42 | 1140.55 | 405.55 | 0.0062 | up |
| (pg/ml) | IL12p70 | 71.57 | 29.42 | 85.66 | 41.91 | 0.0064 | up |
| IP10 | GCSF | 0.85 | 2.28 | 2.24 | 4.24 | 0.0071 | up |
| IL-1α | MCSF | 46.23 | 16.43 | 51.63 | 20.14 | 0.0081 | up |
| IL-2 | TNFα | 167.88 | 40.26 | 183.48 | 48.18 | 0.0083 | up |
| PDGF | sTRAIL | 34.86 | 17.14 | 45.38 | 24.13 | 0.0107 | up |
| IL-7 | IL-5 | 104.52 | 37.85 | 122.31 | 53.26 | 0.0119 | up |
| IL-5 | IL-4 | 11.97 | 3.55 | 13.50 | 4.88 | 0.0142 | up |
| CCL2/MCP1 | IL-13 | 19.44 | 6.91 | 22.17 | 9.51 | 0.0160 | up |
| | IFNγ | 2.86 | 0.77 | 3.24 | 1.31 | 0.0186 | up |
| | FGF | 55.54 | 16.03 | 60.44 | 21.69 | 0.0215 | up |
| | IL-2 | 33.73 | 11.52 | 38.72 | 14.96 | 0.0258 | up |

Group 6 (N = 8)

| Cytokine (pg/ml) | Baseline Mean | Baseline SD | 3 Month Mean | 3 Month SD | pvalue | Direction |
|---|---|---|---|---|---|---|
| IL1RA | 641.91 | 723.71 | 1076.50 | 1024.35 | 0.0182 | up |
| IP10 | 72.78 | 19.68 | 281.60 | 214.98 | 0.0259 | up |
| IL-1α | 39.48 | 13.08 | 57.12 | 17.08 | 0.0369 | up |
| TGFβ | 23.01 | 12.68 | 29.42 | 15.33 | 0.0382 | up |

Note:
P-values were determined using a paired t-test.
*Up = increase in concentration; Down = decrease in concentration.

TABLE 12

Serum biomarkers and respective accession numbers

| Biomarker | Accession Number |
|---|---|
| LIF | NM_002309 |
| IFN-α | NM_024013 |
| IL-1β | NM_000576 |
| IL-8 | NM_000584 |
| CCL2/MCP1 | NM_002982 |
| IL-1RA | NM_001320978 |
| MIP1α | NM_002983 |
| CXCL1/Groα | NM_001511 |
| IL-6 | NM_000600 |
| GCSF | NM_172220 |
| IL-10 | NM_000572 |
| CD40L | NM_000074 |
| IL-17A | NM_002190 |
| IL-17F | NM_052872 |
| IFN-β | NM_002176 |
| CXCL10/IP10 | NM_001565 |

TABLE 12-continued

Serum biomarkers and respective accession numbers

| Biomarker | Accession Number |
|---|---|
| sTRAIL | NM_003810 |
| PAI-1 | NM_000602 |
| CXCL-5 | NM_002994 |
| HGF | NM_000601 |
| NGF | NM_002506 |
| IL-7 | XM_011517522 |
| MIG/CXCL9 | NM_002416 |
| VCAM | NM_001078 |
| TGFβ | NM_000660 |
| ICAM | NM_000201 |
| IL-12p40 | NM_002187 |
| MIP1β | NM_002984 |

What is claimed is:

1. A method for treating a subject with multiple sclerosis comprising:
performing or having performed at least one protein biomarker detection assay on a sample from the subject to determine the expression level of a panel of biomarkers indicating biomarker expression levels in the sample from the subject, the panel of biomarkers comprising IL-1β, IL-8, CCL2/MCP1, IL-1RA, CXCL1/Groα, IL-6, G-CSF, CD40L, IL-17F, IFN-β, and CXCL10/IP10; and
classifying or having classified the subject into at least one of group 1, group 2, group 3, group 4, group 5, and group 6 based on the expression level of the panel of biomarkers as compared to a control profile of biomarker levels in patients with multiple sclerosis;
wherein group 1 is characterized by the sample having higher expression level of only CD40L as compared to the control profile;
wherein group 2 is characterized by the sample having lower or not significantly different expression levels of all biomarkers in the panel of biomarkers as compared to the control profile;
wherein group 3 is characterized by the sample having higher expression levels of IL-8, CXCL1/Groα, IL-1β, IL-1RA, and CCL2/MCP1 in the panel of biomarkers as compared to the control profile;
wherein group 4 is characterized by the sample having higher expression levels of G-CSF and CD40L in the panel of biomarkers as compared to the control profile;
wherein group 5 is characterized by the sample having higher expression levels of CSCL10/IP10 and IL-6 in the panel of biomarkers as compared to the control profile; and
wherein group 6 is characterized by the sample having higher expression levels of IFN-β and IL-17F in the panel of biomarkers as compared to the control profile, and
treating the subject based on the subject's classification into groups 1 to 6
wherein when the subject is classified in group 1 or group 5, the subject is treated with IFN-β alone or in combination with at least one selected from the group consisting of glatiramer acetate, natalizumab, dimethyl fumarate, fingolimod, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, and bone marrow stem cell transplantation therapy;
wherein when the subject is classified in group 3 or group 6, the subject is treated with one of glatiramer acetate, anti-VLA4, dimethyl fumarate, or teriflunomide alone or in combination with at least one selected from the group consisting of fingolimod, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, and bone marrow stem cell transplantation therapy; and
wherein when the subject is classified in group 2 or group 4, the subject is treated either with a combination of IFN-β and one of glatiramer acetate, anti-VLA4, dimethyl fumarate, or teriflunomide, or with a combination of IFN-β and one of fingolimod, a statin, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, and bone marrow stem cell transplantation therapy.

2. The method of claim 1, wherein the at least one biomarker detection assay is a multiplex protein assay.

3. The method of claim 1, wherein the panel of biomarkers further comprises LIF, IFN-α, MIP1α, IL-10, IL-17A, sTRAIL, PAI-1, CXCL5, HGF, NGF, IL-7, MIG/CXCL9, and VCAM.

4. The method of claim 1, wherein the panel of biomarkers comprises eleven biomarkers.

5. The method of claim 1, wherein the sample comprises protein from blood of the subject.

6. The method of claim 1, wherein the sample comprises protein from blood of the subject, the blood of the subject is obtained prior to treatment of the subject with IFN-β.

7. The method of claim 1, wherein the sample comprises protein from blood of the subject, the blood of the subject is obtained 3 months after beginning treatment of the subject with IFN-β.

8. A method for treating a subject with multiple sclerosis comprising:
wherein the subject's expression levels of IL-1β, IL-8, CCL2/MCP1, IL-1RA, CXCL1/Groα, IL-6, G-CSF, CD40L, IL-17F, IFN-β, and CXCL10/IP10 in a sample from the subject have been determined; and
classifying or having classified the subject into at least one of group 1, group 2, group 3, group 4, group 5, and group 6 based on the expression level of the panel of biomarkers as compared to a control profile of biomarker levels in patients with multiple sclerosis;
wherein group 1 is characterized by the sample having higher expression level of only CD40L as compared to the control profile;
wherein group 2 is characterized by the sample having lower or not significantly different expression levels of all biomarkers in the panel of biomarkers as compared to the control profile;
wherein group 3 is characterized by the sample having higher expression levels of IL-8, CXCL1/Groα, IL-1β, IL-1RA, and CCL2/MCP1 in the panel of biomarkers as compared to the control profile;
wherein group 4 is characterized by the sample having higher expression levels of G-CSF and CD40L in the panel of biomarkers as compared to the control profile;

wherein group 5 is characterized by the sample having higher expression levels of CSCL10/IP10 and IL-6 in the panel of biomarkers as compared to the control profile; and wherein group 6 is characterized by the sample having higher expression levels of IFN-β and IL-17F in the panel of biomarkers as compared to the control profile, and treating the subject based on the subject's classification into groups 1 to 6 wherein when the subject is classified in group 1 or group 5, the subject is treated with IFN-β alone or in combination with at least one selected from the group consisting of glatiramer acetate, natalizumab, dimethyl fumarate, fingolimod, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, and bone marrow stem cell transplantation therapy;

wherein when the subject is classified in group 3 or group 6, the subject is treated with one of glatiramer acetate, anti-VLA4, dimethyl fumarate, or teriflunomide alone or in combination with at least one selected from the group consisting of fingolimod, statins, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, and bone marrow stem cell transplantation therapy; and wherein when the subject is classified in group 2 or group 4, the subject is treated either with a combination of IFN-β and one of glatiramer acetate, anti-VLA4, dimethyl fumarate, or teriflunomide, or with a combination of IFN-β and one of fingolimod, a statin, methylprednisolone, methotrexate, cladribine, cyclophosphamide, anti-IFN γ antibody, CTLA4-Ig, anti-CD20 antibody, anti-CD52 antibody, IL-17 inhibitor, IL-23 inhibitor, and bone marrow stem cell transplantation therapy.

* * * * *

UNITED STATES PATENT AND TRADEMARK OFFICE
CERTIFICATE OF CORRECTION

PATENT NO. : 11,740,248 B2
APPLICATION NO. : 15/763056
DATED : August 29, 2023
INVENTOR(S) : Robert C. Axtell and Lawrence Steinman Page 1 of 1

It is certified that error appears in the above-identified patent and that said Letters Patent is hereby corrected as shown below:

In the Specification

Column 1, Line 12, before the paragraph "BACKGROUND" please add the following paragraph:
"STATEMENT OF FEDERALLY FUNDED RESEARCH
This invention was made with government support under NS075099 awarded by the National Institutes of Health. The government has certain rights in the invention."

Signed and Sealed this
Sixth Day of January, 2026

John A. Squires
*Director of the United States Patent and Trademark Office*